(12) United States Patent
Brown et al.

(10) Patent No.: US 11,878,089 B2
(45) Date of Patent: Jan. 23, 2024

(54) THREE-DIMENSIONAL PRINTING OF COLLOIDAL BUILDING BLOCKS FOR WOUND HEALING MATERIALS

(71) Applicant: North Carolina State University, Raleigh, NC (US)

(72) Inventors: Ashley Brown, Raleigh, NC (US); Michael Daniele, Raleigh, NC (US); Jeremy Nortey, Raleigh, NC (US); Daniel Chester, Raleigh, NC (US); Terrika Ngobili, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 467 days.

(21) Appl. No.: 17/045,373

(22) PCT Filed: Apr. 5, 2019

(86) PCT No.: PCT/US2019/025992
§ 371 (c)(1),
(2) Date: Oct. 5, 2020

(87) PCT Pub. No.: WO2019/195681
PCT Pub. Date: Oct. 10, 2019

(65) Prior Publication Data
US 2021/0162097 A1   Jun. 3, 2021

Related U.S. Application Data

(60) Provisional application No. 62/653,304, filed on Apr. 5, 2018.

(51) Int. Cl.
| | |
|---|---|
| *A61L 27/26* | (2006.01) |
| *B33Y 10/00* | (2015.01) |
| *B33Y 70/00* | (2020.01) |
| *B29C 64/112* | (2017.01) |
| *A61L 26/00* | (2006.01) |
| *A61L 27/38* | (2006.01) |
| *A61L 27/52* | (2006.01) |
| *B33Y 80/00* | (2015.01) |
| *B29K 105/00* | (2006.01) |
| *B29L 31/00* | (2006.01) |

(52) U.S. Cl.
CPC ............ *A61L 27/26* (2013.01); *A61L 26/008* (2013.01); *A61L 26/0052* (2013.01); *A61L 27/3804* (2013.01); *A61L 27/52* (2013.01); *B29C 64/112* (2017.08); *B33Y 10/00* (2014.12); *B33Y 70/00* (2014.12); *A61L 2300/802* (2013.01); *A61L 2400/12* (2013.01); *B29K 2105/0061* (2013.01); *B29K 2995/0056* (2013.01); *B29L 2031/753* (2013.01); *B33Y 80/00* (2014.12)

(58) Field of Classification Search
CPC .... A61L 27/26; A61L 26/0052; A61L 26/008; A61L 27/3804; A61L 27/52; A61L 2300/802; A61L 2400/12; B33Y 10/00; B33Y 70/00; B33Y 80/00; B29C 64/112; B29K 2105/0061; B29K 2995/0056; B29L 2031/753

See application file for complete search history.

(56) References Cited

U.S. PATENT DOCUMENTS

| | | | |
|---|---|---|---|
| 10,442,182 B2 | 10/2019 | Varanasi et al. | |
| 2017/0143831 A1 | 5/2017 | Varanasi et al. | |
| 2017/0216498 A1* | 8/2017 | Kang | ...................... A61L 27/50 |

FOREIGN PATENT DOCUMENTS

CN    106581762 A   *   4/2017

OTHER PUBLICATIONS

Bachman et al. "Ultrasoft, highly deformable microgels," Soft Matter, 11(10), pp. 2018-2028 (2015).
Bhatia et al. "New Approach to Producing Patterned Biomolecular Assemblies," Journal of the American Chemical Society, 114(11), pp. 4432-4433 (1992).
Castro et al. "Design of a Novel 3D Printed Bioactive Nanocomposite Scaffold for Improved Osteochondral Regeneration," Author manuscript, 29 pages, Published in final edited form as: Cellular and molecular bioengineering, 8(3): pp. 416-432 (2015).
Chadwick et al. "Measurements of intestinal permeability using low molecular weight polyethylene glycols (PEG 400)," I. Chemical analysis and biological properties of PEG 400, Gastroenterology, 73(2), pp. 241-246 (1977).
Chen et al. "Geometric Control of Cell Life and Death," Science, 276(5317), pp. 1425-1428 (1997).
Chester et al., "Ultrasonic Microplotting of Microgel Bioinks," ACS Applied Materials & Interfaces, 12, pp. 47309-47319 (2020).
Christman et al. "Protein Micropatterns Using a pH-Responsive Polymer and Light," Langmuir, 21(18), pp. 8389-8393 (2005).

(Continued)

*Primary Examiner* — Shirley V Gembeh
(74) *Attorney, Agent, or Firm* — Jenkins, Taylor & Hunt, P.A.

(57) ABSTRACT

Bio-ink compositions comprising bio-compatible microgels or nanogels are described. The bio-inks can comprise, for example, micro- or nanogels comprising crosslinked poly (N-isopropylacrylamide) (poly-NIPam). The bio-inks can further comprise viscosity control agents, such as poly (ethylene glycol) (PEG), and/or surface tension agents. Three-dimensional (3D) printing (e.g., piezoelectric printing) of the bio-inks can provide 3D printed materials comprising microgel or nanogel assemblies of the bio-ink compositions. These materials can be used as scaffolds for preparing biological tissues for use, for instance, in regenerative medicine.

14 Claims, 13 Drawing Sheets

(56) References Cited

OTHER PUBLICATIONS

Christman et al., "Submicron Streptavidin Patterns for Protein Assembly," Langmuir, 22(17), pp. 7444-7450 (2006).
Crowther et al. "Poly(NIPAM) microgel particle de-swelling: a light scattering and small-angle neutron scattering study," Colloids and Surfaces A: Physicochemical and Engineering Aspects, 152(3), pp. 327-333 (1999).
Debord et al. "Synthesis and characterization of pH-responsive copolymer microgels with tunable volume phase transition temperatures," Langmuir, 19(18), pp. 7662-7664 (2003).
Dietsch et al., "Soft Nanotechnology—from Colloid Physics to Nanostructured Functional Materials," CHIMIA International Journal for Chemistry, 62(10), pp. 805-814 (2008).
Dietze et al. "Rapid prototyping of microfluidic chips for dead-volume free MS coupling," Analytical and Bioanalytical Chemistry, 407(29), pp. 8735-8743 (2015).
Dowding et al. "Preparation and Swelling Properties of Poly(NIPAM) "Minigel" Particles Prepared by Inverse Suspension Polymerization," Journal of Colloid and Interface Science, 221(2), pp. 268-272 (2000).
Xiong et al. "Dual temperature/pH-sensitive drug delivery of poly(N-isopropylacrylamide-co-acrylic acid) nanogels conjugated with doxorubicin for potential application in tumor hyperthermia therapy," Colloids Surf B Biointerfaces, Jun 1; 84(2), pp. 447-453 (2011).
Erim et al. "Performance of a physically adsorbed high-molecular-mass polyethyleneimine layer as coating for the separation of basic proteins and peptides by capillary electrophoresis," Journal of Chromatography A, 708(2), pp. 356-361 (1995).
Falconnet et al. "Surface engineering approaches to micropattern surfaces for cell-based assays," Biomaterials, 27(16), pp. 3044-3063 (2006).
Fan et al. "Surface modification with BSA blocking based on in situ synthesized gold nanoparticles in poly(dimethylsiloxane) microchip," Colloids and Surfaces B: Biointerfaces, 75(2), pp. 608-611 (2010).
Ferris et al. "Bio-ink for on-demand printing of living cells," Biomaterials Science, 1(2), pp. 224-230 (2013).
Fink et al. "Comparative study and improvement of current cell micro-patterning techniques," Royal Society of Chemistry, Apr. 30, 2007, pp. 672-680., doi: 10.1039/b618545b. Accessed Aug. 18, 2017.
Hahn et al. "Three-dimensional biochemical and biomechanical patterning of hydrogels for guiding cell behavior," Advanced Materials, 18(20), pp. 2679-2684 (2006).
Hu et al. "Polyethyleneimine functionalized single-walled carbon nanotubes as a substrate for neuronal growth," The Journal of Physical Chemistry B, 109(10), pp. 4285-4289 (2005).
Bradley et al. "Interaction of Nonionic Surfactants with Copolymer Microgel Particles of NIPAM and Acrylic Acid," Langmuir, 21(19), pp. 8630-8634 (2005).
International Preliminary Report on Patentability corresponding to International Application No. PCT/US2019/025992 dated Oct. 6, 2020.
International Search Report and Written Opinion of the International Searching Authority corresponding to International Application No. PCT/US 2019/025992 dated Jun. 24, 2019.
Su et al. "iRGD-coupled responsive fluorescent nanogel for targeted drug delivery," Biomaterials, Apr; 34(13), pp. 3523-3533 (2013).
Jeyachandran et al. "Efficiency of blocking of non-specific interaction of different proteins by BSA adsorbed on hydrophobic and hydrophilic surfaces," Journal of colloid and interface science, 341(1), pp. 136-142 (2010).
Jones et al. "Stem cell patterning and fate in human epidermis," Cell, 80(1), pp. 80, 83-93 (1995).
Kamperman et al. "Single Cell Microgel Based Modular Bioinks for Uncoupled Cellular Micro- and Macroenvironments," Advanced Healthcare Materials, 6(3), 1600913, 9 pages, doi: 10.1002/adhm.201600913 (2016).

Karg et al. "New 'smart' poly(NIPAM) microgels and nanoparticle microgel hybrids: properties and advances in characterization," Current Opinion in Colloid & Interface Science, 14(6), pp. 438-450 (2009).
Kharkar et al. "Designing degradable hydrogels for orthogonal control of cell microenvironments," Chemical Society Reviews, 42(17), pp. 7335-7372 (2013).
Kim et al. "Polymer microstructures formed by moulding in capillaries," Nature, 376(6541), pp. 581-584 (1995).
Kim et al. "Development of hydroxyapatite bone scaffold for controlled drug release via poly(€-caprolactone) and hydroxyapatite hybrid coatings," Journal of Biomedical Materials Research Part B: Applied Biomaterials, 70(2), pp. 240-249 (2004).
Krebs et al. "Formation of Ordered Cellular Structures in Suspension via Label-Free Negative Magnetophoresis," Nano Letters, 9(5), pp. 1812-1817 (2009).
Kumar et al. "Molecular engineering of supramolecular scaffold coatings that can reduce static platelet adhesion," Journal of the American Chemical Society, 130(4), p. 1466 (2008).
Lanzalaco et al., "Poly(N-isopropylacrylamide) and Copolymers: A Review on Recent Progresses in Biomedical Applications," Gels, vol. 3, p. 36, (2017).
Larson et al. "Controlled deposition of picoliter amounts of fluid using an ultrasonically driven micropipette," Review of scientific instruments, 75(4), pp. 832-836 (2004).
Lee et al. "Protein Nanoarrays Generated By Dip-Pen Nanolithography," Science, 295(5560), pp. 1702-1705 (2002).
Li et al. "3D-printed biopolymers for tissue engineering application," International Journal of Polymer Science, vol. 2014, Article ID 829145, 13 pages (2014).
Low et al. "Evaluation of mammalian cell adhesion on surface-modified porous silicon," Biomaterials, 27(26), pp. 4538-4546 (2006).
Massia et al. "Covalently Attached GRGD on Polymer Surfaces Promotes Biospecific Adhesion of Mammalian Cellsa," Annals of the New York Academy of Sciences, 589(1), pp. 261-270 (1990).
Moselhy et al. "In vitro studies of the interaction of poly(NIPAM/MAA) nanoparticles with proteins and cells," Journal of Biomaterials Science, Polymer Edition, 11(2), pp. 123-147 (2000).
Murphy et al. "3D bioprinting of tissues and organs," Nature biotechnology, 32(8), pp. 773-785 (2014).
Murray et al. "The preparation, characterisation and applications of colloidal microgels," Advances in colloid and interface science, 54, pp. 73-91 (1995).
Nichol et al. "Modular tissue engineering: engineering biological tissues from the bottom up," Author manuscript, 17 pages, published in final edited form as: Soft Matter, 5(7), pp. 1312-1319 (2009). http://doi.org/10.1039/b814285h.
Nicolau et al., "Micron-Sized Protein Patterning on Diazonaphthoquinone/Novolak Thin Polymeric Films," Langmuir, 14(7), pp. 1927-1936 (1998).
Nortey et al., "3D Printing of Colloidal Building Blocks for Modular Tissue Engineering," Abstract of Poster Presentation, 2017 Annual Meeting of the Society for Biomaterials, Minneapolis, Minnesota, 1 page, Apr. 6, 2017.
O'Brien "Biomaterials & scaffolds for tissue engineering," Materials Today, 14(3), pp. 88-95 (2011).
Odde et al. "Laser-guided direct writing of living cells," Biotechnology and Bioengineering, 67(3), pp. 312-318 (2000).
Prime et al. "Self-assembled organic monolayers: model systems for studying adsorption of proteins at surfaces," Science, 252(5009), pp. 1164-1167 (1991).
Ramsden et al. "Immobilization of proteins to lipid bilayers," Biosensors and Bioelectronics, 11(5), pp. 523-528 (1996).
Roth et al. "Inkjet printing for high-throughput cell patterning," Biomaterials, 25(17), pp. 3707-3715 (2004).
Saunders et al. "Microgel particles as model colloids: theory, properties and applications," Advances in colloid and interface science, 80(1), pp. 1-25 (1999).
Saxena et al. "Microgel mechanics in biomaterial design," Accounts of chemical research, 47(8), pp. 2426-2434 (2014).

(56) References Cited

OTHER PUBLICATIONS

Shin et al. "A Bioactive Carbon Nanotube-Based Ink for Printing 2D and 3D Flexible Electronics," Advanced Materials, pp. 3280-3289 (2016).
Sigal et al. "Effect of Surface Wettability on the Adsorption of Proteins and Detergents," Journal of the American Chemical Society, 120(14), pp. 3464-3473 (1998).
Sirringhaus et al. "High-resolution inkjet printing of all-polymer transistor circuits," Science, 290(5499), pp. 2123-2126 (2000).
Su et al. "Microgel-Based Inks for Paper-Supported Biosensing Applications," Biomacromolecules, 9(3), pp. 935-941 (2008).
Thorne et al. "Microgel applications and commercial considerations," Colloid and Polymer Science, 289(5), pp. 625-646 (2011).
Tibbitt et al. "Hydrogels as extracellular matrix mimics for 3D cell culture," Biotechnology and Bioengineering, 103(4), pp. 655-663 (2009).
Whitaker "The history of 3D printing in healthcare," The Bulletin of the Royal College of Surgeons of England, 96(7), 3 pages (2014).
Xia et al. "Polyethyleneimine coating enhances the cellular uptake of mesoporous silica nanoparticles and allows safe delivery of siRNA and DNA constructs," ACS nano, 3(10), pp. 3273-3286 (2009).
Xiao et al. "Enzyme-Linked Immunosorbent Assay (ELISA) and Blocking with Bovine Serum Albumin (BSA)—Not all BSAs are alike," Author manuscript, 6 pages, published in final edited form as: Journal of immunological methods, 384(1-2), pp. 148-151 (2012).
Zhang et al. "Biological surface engineering: a simple system for cell pattern formation," Biomaterials, 20(13), pp. 1213-1220 (1999).
Zhang et al. "Novel chemical surface modification to enhance hydrophobicity of polyamide-imide (PAI) hollow fiber membranes," Journal of membrane science, 380(1), pp. 241-250 (2011).
Zhou et al. "Surface Modification for PDMS-Based Microfluidic Devices," Electrophoresis, 33(1), pp. 89-104 (2012).

\* cited by examiner

THREE-DIMENSIONAL PRINTING OF COLLOIDAL BUILDING BLOCKS FOR WOUND HEALING MATERIALS

CROSS-REFERENCE TO RELATED APPLICATION

This application claims the benefit of U.S. Provisional Patent Application Ser. No. 62/653,304, filed Apr. 5, 2018, the disclosure of which is incorporated herein by reference in its entirety.

TECHNICAL FIELD

The presently disclosed subject matter relates to bio-ink compositions comprising bio-compatible microgels or nanogels, as well as three-dimensional (3D) printed materials comprising microgel or nanogel assemblies of the bio-ink compositions. The presently disclosed subject matter further relates to methods of preparing 3D biomaterial scaffolds using the bio-ink compositions and the 3D scaffolds prepared thereby, as well as methods of preparing biological tissues by contacting the scaffolds with biological cells.

ABBREVIATIONS

%=percent or percentage
μm=micrometer or micron
3D=three dimensional
AAc=acrylic acid
APS=ammonium persulfate
APTMS=(3-aminopropyl)triethoxysilane
BIS=N,N-methylenebisacrylamide
BSA=bovine serum albumin
Da=Dalton
DDAO=[7-hydroxy-9H-(1,3-dichloro-9,9-dimethylacridine-2-one)]
DiH$_2$O=deionized water
FBS=fetal bovine serum
HMDS=hexamethyldisilazane
kDa=kilodalton
LbL=layer-by-layer
mg=milligram
ml=milliliter
mm=millimeter
mM=millimolar
Mw=weight average molecular weight
nHDF=neonatal human dermal fibroblasts
NIPam=N-isopropylacrylamide
nm=nanometer
Pa=pascal
PBS=phosphate buffered saline
PEG=polyethylene glycol
PEI=polyethylenimine
RPM=revolutions per minute
SDS=sodium dodecyl sulfate
vol=volume

BACKGROUND

The ability to fabricate replacement human organs from autologous cells is an important goal of regenerative medicine. Micropatterning of biomaterials at a sub-cellular level can be a starting point for modular tissue engineering that can provide for the creation of microarchitectures that can be built into organized three-dimensional (3D) patterns to control cellular adhesion and attachment. Modular tissue engineering is a bottom-up approach to engineering biological tissues that can be used to aid in the repair and replacement of damaged tissues. See Nortey et al., "3D Printing of Colloidal Building Blocks for Modular Tissue Engineering"; Poster Presentation, 2017 Annual Meeting of the Society for Biomaterials, Minneapolis, Minnesota, Apr. 6, 2017. Modular tissue engineering is advantageous over the traditional top-down approach because it allows for the recreation of intricate microstructural features of tissues, which gives exact control over cell behavior at varying scales.

However, there remains a need for additional methods of preparing biological tissues via modular tissue engineering and for additional materials for use in those methods. In particular, there is an ongoing need for additional colloidal bio-ink formulations for use in areas such as but not limited to printing nanogel assemblies for use in modular tissue engineering, for applications related to regenerative medicine, drug delivery studies, and microfluidic research, and in the development of organoids and microtissues). There is also an ongoing need for improved methods for creating defined scaffolds with nanoscale features.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a bio-ink composition comprising: (a) a bio-compatible micro- or nanogel; (b) a liquid carrier; (c) 0 volume (vol) % to 50 vol % of a viscosity control agent; and (d) 0 vol % to 50 vol % of a surface tension control agent; optionally wherein the bio-ink composition comprises 0.1 mg/ml to 100 mg/ml of the micro- or nanogel. In some embodiments, the bio-compatible micro- or nanogel comprises a poly(N-isopropylacrylamide) (poly-NIPam) polymer, optionally wherein the poly-NIPam polymer is a copolymer of N-isopropylacrylamide, acrylic acid, and a crosslinking agent, further optionally wherein the crosslinking agent is N,N-methylenebisacrylamide (BIS) and/or cystamine bisacrylamide. In some embodiments, the poly-NIPam polymer comprises a monomeric content comprising about 40% to 100% N-isopropylacrylamide (NIPam), 0% to 30% acrylic acid, and 0% to 30% BIS, optionally wherein the monomeric content comprises about 90% NIPam, further optionally wherein the monomeric content comprises about 4% BIS.

In some embodiments, the bio-ink composition comprises between about 0.2 mg/ml and about 2 mg/ml of the bio-compatible micro- or nanogel, optionally wherein the bio-ink composition comprises about 2 mg/ml of the bio-compatible microgel. In some embodiments, the bio-compatible micro- or nanogel has an average swollen particle diameter of between about 100 nanometers (nm) and about 10 microns (μm), optionally wherein the average swollen particle diameter is between about 500 nm and about 700 nm.

In some embodiments, the viscosity control agent comprises one or more agent selected from the group comprising a poly(ethylene glycol) (PEG), a polysaccharide, a glucosaminoglycan, glycerol, albumin, collagen, laminin, fibronectin, and elastin. In some embodiments, the viscosity control agent is a PEG, optionally wherein the PEG has a weight average molecular weight ($M_w$) between about 100 Da and about 8,000 kDa, optionally wherein the PEG is $PEG_{400}$. In some embodiments, the bio-ink composition comprises at least between about 5 vol % PEG and about 30 vol % PEG. In some embodiments, the bio-ink composition comprises between about 10 vol % PEG and about 20 vol % PEG.

In some embodiments, the surface tension agent comprises one or more agent selected from the group comprising a surfactant and an ionic liquid, optionally wherein the surfactant is selected from sodium dodecyl sulfate (SDS), hexamethyldisilazane (HMDS), [7-hydroxy-9H-(1,2-dichloro-9,9-dimethylacridin-2-one)] (DDOA), and a sorbitan ester. In some embodiments, the liquid carrier comprises one of the group comprising water, saline, phosphate buffered saline (PBS), and cell culture media. In some embodiments, the bio-ink composition further comprises one or more additional component selected from the group comprising a metabolite, a growth factor, a cytokine, a chemokine, a CD antigen, neurotrophin, a hormone, an enzyme, a viral antigen, a bacterial antigen, a recombinant protein, a natural protein, a monoclonal antibody, a polyclonal antibody, a donor blood serum protein, a donor blood plasma protein, an antimicrobial agent, a small molecule drug, and a cell.

In some embodiments, the presently disclosed subject matter provides a 3D material comprising one or more micro- or nanogel assemblies of a bio-ink composition comprising: (a) a bio-compatible micro- or nanogel; (b) a liquid carrier; (c) 0 vol % to 50 vol % of a viscosity control agent; and (d) 0 vol % to 50 vol % of a surface tension control agent; optionally wherein the bio-ink composition comprises 0.1 mg/ml to 100 mg/ml of the micro- or nanogel. In some embodiments, one or more of the one or more micro- or nanogel assemblies are in contact with a substrate material selected from the group comprising cellulose-based materials, nanofiber-based materials, polyethylene vinyl acetate, a polyester, a polyurethane and glass. In some embodiments, the 3D material is provided in the form of a bandage, a suture, a surgical implant, or a wound dressing.

In some embodiments, the presently disclosed subject matter provides a method of preparing a 3D biomaterial scaffold, wherein said biomaterial scaffold comprises a micro- or nanogel assembly, the method comprising: (a) providing one or more bio-ink composition comprising: a bio-compatible micro- or nanogel; a liquid carrier; 0 vol % to 50 vol % of a viscosity control agent; and 0 vol % to 50 vol % of a surface tension control agent; optionally wherein the bio-ink composition comprises 0.1 mg/ml to 100 mg/ml of the micro- or nanogel; and (b) printing the one or more bio-ink composition in a pre-determined pattern to form a printed layer. In some embodiments, the printing of step (b) comprises the use of a piezo-drop/ultrasound printing technique. In some embodiments, the printing of step (b) comprises the use of a microplotter, optionally an ultrasonic microplotter. In some embodiments, step (b) comprises printing the one or more bio-ink composition from a glass capillary write-head (i) droplet-by-droplet or (ii) in a continuous line or arc, optionally wherein said glass capillary write-head has a tip diameter between about 5 microns and about 30 microns.

In some embodiments, step (b) comprises printing the one or more bio-ink composition in a pre-determined pattern on a bio-compatible substrate or sacrificial substrate, optionally wherein the substrate comprises glass. In some embodiments, the substrate is a chemically cleaned glass or a glass coated with a coating agent selected from the group comprising poly(ethyleneimine) (PEI), bovine serum albumin (BSA), and (3-aminopropyl)trimethoxysilane), optionally wherein the substrate is glass coated with PEI. In some embodiments, the method further comprises printing the one or more bio-ink composition in a second pre-determined pattern to form a second printed layer, wherein said second printed layer is at least partially in contact with the printed layer from step (b); and optionally printing the one or more bio-ink composition in one or more additional predetermined pattern to form one or more additional printed layer, wherein each additional printed layer is at least partially in contact with a previously printed printed layer.

In some embodiments, the presently disclosed subject matter provides a 3D biomaterial scaffold prepared according to a method comprising: (a) providing one or more bio-ink composition comprising: a bio-compatible micro- or nanogel; a liquid carrier; 0 vol % to 50 vol % of a viscosity control agent; and 0 vol % to 50 vol % of a surface tension control agent; optionally wherein the bio-ink composition comprises 0.1 mg/ml to 100 mg/ml of the micro- or nanogel; and (b) printing the one or more bio-ink composition in a pre-determined pattern to form a printed layer. In some embodiments, the scaffold has one or more features having a length and/or width of less than about 50 nm, optionally wherein the scaffold has one or more features having a length and/or width of between about 5 nm and about 30 nm, optionally wherein the scaffold has one or more features having a length and/or width of between about 5 nm and about 10 nm. In some embodiments, the scaffold has a layer height of between about 50 nm and about 2 µm, optionally wherein the layer height is about 400 nm. In some embodiments, the scaffold comprises two or more layers of printed material. In some embodiments, the scaffold comprises a mechanical or topological gradient.

In some embodiments, the presently disclosed subject matter provides a method of preparing a biological tissue; the method comprising: (a) providing one or more 3D biomaterial scaffolds prepared according to a method comprising: (i) providing one or more bio-ink composition comprising: a bio-compatible micro- or nanogel; a liquid carrier; 0 vol % to 50 vol % of a viscosity control agent; and 0 vol % to 50 vol % of a surface tension control agent; optionally wherein the bio-ink composition comprises 0.1 mg/ml to 100 mg/ml of the micro- or nanogel; and (ii) printing the one or more bio-ink composition in a pre-determined pattern to form a printed layer; and (b) contacting the one or more scaffolds with a composition comprising one or more types of biological cells. In some embodiments; the composition comprising one or more types of cells comprises dermal fibroblasts, optionally neonatal human dermal fibroblasts.

In some embodiments, the composition comprising one or more types of biological cells is an ex vivo cell composition and the method further comprises (c) culturing the cells while they remain in contact with the one or more scaffolds, thereby preparing a biological tissue, wherein said biological tissue has an architecture based on the shape of the 3D biomaterial scaffold, and optionally transferring said biological tissue to a subject in need of tissue replacement and/or regeneration. In some embodiments, the subject is in need of wound healing.

In some embodiments, the composition comprising one or more types of biological cells is an in vivo cell composition and step (b) comprises implanting the one or more scaffolds in a subject in need of tissue replacement and/or regeneration. In some embodiments, the subject is in need of wound healing.

Accordingly, it is an object of the presently disclosed subject matter to provide bio-ink compositions, biomaterial scaffolds comprising microgel and/or nanogel assemblies and methods for making the same, and methods of preparing biological tissues using the scaffolds.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

DETAILED DESCRIPTION

Figure 1A:
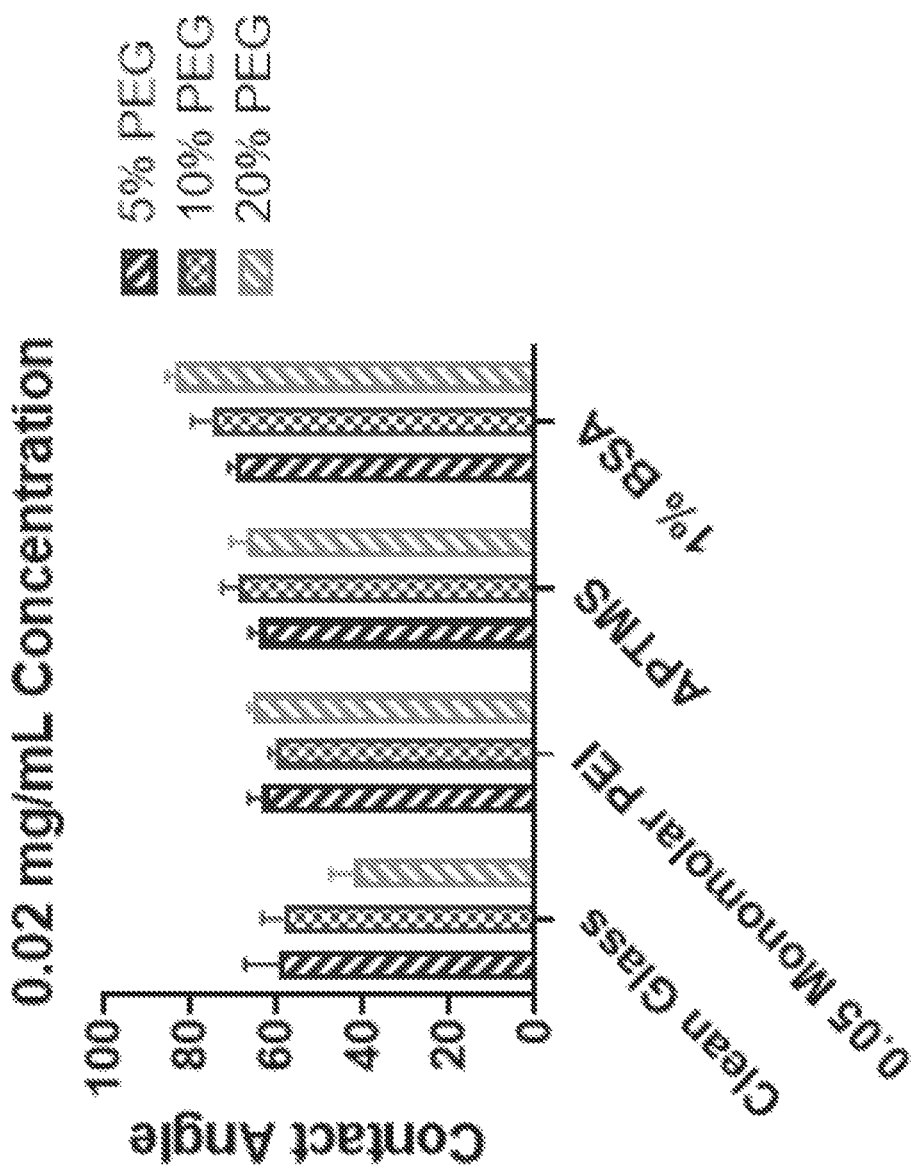
FIG. 1A is a graph showing the contact angle measurements of a microgel bio-ink comprising 0.02 milligrams per milliliter (mg/ml) of a poly(N-isopropylacrylamide) (poly-NIPam) microgel prepared using 4 percent (%) N,N'-methylenebis(acrylamide) (BIS) and further containing varying amounts of polyethylene glycol (PEG) printed on surfaces with different coatings. The different surfaces are as described on the x-axis: clean glass, glass treated with 0.5 monomolar polyethylenimine (PEI), (3-aminopropyl)triethoxysilane (APTMS), or 1% bovine serum albumin (BSA). For each surface, results are shown (from left to right) for a bio-ink comprising 5% PEG (black diagonal striped bars), 10% PEG (checker board bars), or 20% PEG (grey diagonal striped bars).

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "bio-ink" as used herein refers to a composition that can be deposited (e.g., on a substrate via a 3D printing technique or other printing technique) and that is capable of supporting cell adhesion, viability, and/or proliferation.

The terms "nanoparticle" and "nanoparticulate" as used herein refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm).

The terms ""microparticle" and "microparticulate" as used herein refer to a structure having at least one region with a dimension (e.g., length, width, diameter, etc.) of less than about 1,000 μm. In some embodiments, the dimension is smaller (e.g., about 500 μm, about 250 μm, about 200 μm, about 150 μm, about 125 μm, about 100 μm, about 80 μm, about 70 μm, about 60 μm, about 50 μm, about 40 μm, about 30 μm, about 20 μm, or about 10 μm).

The micro- or nanoparticles can have any three-dimensional shape. In some embodiments, the particles are approximately spherical. In some embodiments, the particles are disc, cube or rod shaped. In some embodiments, the particles are irregularly shaped.

More particularly, the terms "nanogel" and "microgel" as used herein typically refer to a colloidal hydrogel in the nanoparticulate or microparticulate scale. In some embodiments, the term "micro- or nanogel" refers to a colloidal hydrogel comprising micro- and/or nanoparticles with a swollen particulate size between about 10 nm and about 100 microns or between about 100 nm and about 10 microns. In some embodiments, the microgel is composed of three major components: a crosslinker, a main monomer, and a functional "handle" (i.e., a functional monomer).

In some embodiments, the micro- or nanogel is a crosslinked poly(N-isopropylacrylamide) copolymer, i.e., a copolymer prepared from N-isopropylacrylamide (NIPam) and at least one other monomer. Typically, the monomeric composition of the copolymer comprises at least about 40% NIPam (i.e., wherein the monomeric content of the copolymer is at least about 40% from NIPam). In some embodiments, the monomeric composition comprises at least about, 45, 50, 55, 60, 65, 70, 75, 80, 85, 86, 87, 88, 89, 90, 91, 92, 93, 94, or 95% or more NIPam. In some embodiments, the micro- or nanogel comprises NIPam as the main monomer (e.g., the component present in the highest percentage), N,N-methylenebis(acrylamide) (BIS) or cystamine bisacrylamide as the crosslinker, and acrylic acid or another functionalized vinyl monomer as the functional handle.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering (DLS).

As used herein, a "macromolecule" refers to a molecule of high relative molecular mass, the structure of which comprises the multiple repetition of units derived from molecules of low relative molecular mass, e.g., monomers and/or oligomers.

An "oligomer" refers to a molecule of intermediate relative molecular mass, the structure of which comprises a small plurality (e.g., 2, 3, 4, 5, 6, 7, 8, 9, or 10) of repetitive units derived from molecules of lower relative molecular mass.

As used herein, a "monomer" refers to a molecule that can undergo polymerization, thereby contributing constitutional units, i.e., an atom or group of atoms, to the essential structure of a macromolecule.

The terms "polymer" and "polymeric" refer to chemical structures that have repeating constitutional units (i.e., multiple copies of a given chemical substructure or "monomer unit" or "monomeric" units). As used herein, polymers can refer to groups having more than 10 repeating units and/or to groups wherein the repeating unit is other than methylene.

Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), carboxylic acids, esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions (e.g., at a certain pH present in vivo or in the presence of enzymes).

A "copolymer" refers to a polymer derived from more than one species of monomer. Each species of monomer provides a different species of monomer unit.

As used herein, a "random copolymer" refers to a copolymer wherein the different species of monomer units are arranged in any order. In some embodiments, the random copolymer monomer units are arranged in an order that has no recognizable pattern. The ratio of one monomer unit to another can depend upon a number of factors, e.g., the reactivity of the different monomers and/or other polymerization conditions (e.g., temperature, relative amounts of starting materials, the order of starting material addition, solvent, etc.).

Polydispersity (PDI) refers to the ratio ($M_w/M_n$) of a polymer sample. $M_w$ refers to the mass average molar mass (also commonly referred to as weight average molecular weight). $M_n$ refers number average molar mass (also commonly referred to as number average molecular weight).

"Biocompatible" as used herein, generally refers to a material and any metabolites or degradation products thereof that are generally non-toxic to a biological organism, tissue, or cell, and which do not cause any significant adverse effects to the biological organism, tissue, or cell.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks. In some embodiments, the degradation time is longer, e.g., a year or years.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The term "amphiphilic" refers to a molecule or polymer that contains both hydrophilic and hydrophobic groups.

The terms "cross-linking agent" or "crosslinker" refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., two different polymer chains) or to link two groups on the same entity (e.g., a single polymer chain) to form a cross-linked composition. Generally, as used herein, the term "cross-linked" refers to a composition comprising multiple bonds or linkages between two entities or comprising multiple added bonds or linkages between groups on the same entity.

The term "ultrasonic" when used with regard to printing refers to a fluid dispensing method wherein a small alternating current is driven along a piezoelectric element, causing a light vibration throughout an attached micropipette. The vibration causes a fluid in the micropipette to be dispensed, e.g., causing the fluid to wick to a surface located under the micropipette tip.

The term "sacrificial" as used herein refers to a component that is not intended for use in a final product that comes into contact with a living subject (e.g., an implant comprising a micro- or nanogel assembly or bioengineered tissue) but is used during at least a portion of a method of production in the final product.

The term "wound" as used herein can refer to an injury to living tissue. In some embodiments, the term refers to an injury where the skin is cut or damaged. Wounds can result from any cause, both accidental and non-accidental, e.g., a surgical incision, a fall or other external violence to the subject, disease, e.g., a skin disease, or an infection. Thus, wounds include, but are not limited to cuts, lacerations, lesions, etc.

II. Bio-Ink Compositions, Materials Prepared Therefrom, and Related Methods

An aim of the regenerative medicine field is to restore the original form and function of a damaged tissue and there have been numerous investigations into techniques of the creation of a synthetic material scaffold that can fulfill this role. The purpose of these material scaffolds is to not only to provide a structure in which the regenerative process can take place, but to also participate in the regenerative process by providing extracellular cues to invading cells. Such cues can include the scaffold's mechanics, the scaffold's topography, and the inclusion of bio-active agents in the scaffold. How finely these parameters can be controlled can vary in degree based on the type of material used and the method used to create the scaffold.

Synthetic polymers are commonly used for the creation of scaffolds that are designed to mimic soft tissues for use in regenerative engineering applications due to the ease by which their mechanical, physical, and chemical properties can be controlled; low batch to batch variability; and low cost of production. One exemplary polymer for use in preparing scaffolds is poly(N-isopropylacrylamide) (poly-NIPam). Poly-NIPam has the ability to create small, colloidally stable hydrogel particles, termed microgels, when synthesized in a precipitation-polymerization reaction. Microgels offer the advantage of having higher degrees of tunability compared to bulk hydrogels. By simply changing the amounts of the constituents used to make the microgel particles, the size, mechanics, and structure of the particle can be controlled. Microgel particles can also be made into bioactive particles by covalently coupling proteins, antibodies, or growth factors to the polymeric backbone of the particle.

Microgels can be made into thin films through a layer-by-layer (LbL) centrifugation process. Films comprising microgels offer the advantages of having material properties over several different length scales that cells are able to interact with. On the macroscale, microgel films have bulk mechanical properties, such as Young's Modulus, that are similar to bulk hydrogels made of other polymers. However, since microgel films comprise individually polymerized hydrogel particles, they also have microscale, time dependent mechanical properties, such as viscosity, that act over time scales similar to what is found in native biological tissues. When combined, both the macroscale and microscale properties of microgel films create a scaffold that more accurately mimics a cell's native environment as compared to traditional scaffolds made from other polymers. Combined with the ability of covalently coupling bioactive agents to individual particles, microgel films offer a wide range of properties that can be controlled in order to create a material scaffold that accurately mimics a desired environment.

A limitation of creating microgel films using the traditional LbL centrifugation method is that it is currently not possible to make a scaffold composed of distinct areas of multiple formulations of microgel particles. Since centrifugation is the main mode by which the microgel particles are deposited onto the surface that the scaffold is to be built on, there is no possible way to spatially control the location of where specific microgel formulations will be deposited. Biological tissues are not uniform in their material properties, so having spatial control over where different microgel formulations are deposited is desirable when creating a scaffold that accurately mimics native tissue. The ability to spatially control microgel particle deposition can also lead to the creation of patterned material scaffolds that can be used to study how certain material properties can influence cellular behavior.

For other material platforms, 3D printing has been used as a technique for the creation of scaffolds with highly defined architectures. One main 3D printing technique is ink-jet printing, which uses either heat or pressure in order to deposit materials onto a surface in a highly controlled fashion. However, biological materials are highly sensitive to changes in pressure and temperature, so the use of this technique for regenerative medicine applications is limited. On the other hand, piezoelectric printing offers the same spatial control and resolution as ink-jet printing, but without the need of high temperatures and pressures and instead uses a small alternating current to vibrate the printhead, leading to the print material being deposited onto the surface. This makes piezoelectric printing a particularly suitable technique for printing biological materials in a highly controllable fashion to create scaffolds with highly defined properties and to overcome the issues presented by the traditional LbL technique. According to one aspect of the presently disclosed subject matter, microgel solutions with added thickening agents are printed on surfaces with different coatings, contact angles, and surface charges.

Accordingly, in some embodiments, the presently disclosed subject matter provides, colloidal micro- or nanogels with finely controlled mechanical and bioactive properties as building blocks for creating tissue-engineered scaffolds. In some embodiments, 3D printing is used to combine the micro- or nanogel bio-ink building blocks into 3D structures with well-defined micro- and nanoscale features. These structures can thus have more control over nanoscale architecture than bulk gels prepared from the same polymers.

In some embodiments, the presently disclosed subject matter relates to the use of piezo-drop/ultrasound printing with the presently disclosed bio-inks. Nanogel thin films are routinely created through a layer-by-layer (LbL) process and have shown that film mechanical properties, such as, but not limited to, elastic modulus, loss tangent, shear modulus, and viscoelasticity, can direct cell adhesion and spreading responses. As disclosed herein, 3D printing of micro- or nanogel compositions can facilitate the creation of films with defined patterns, which is not currently achievable through LbL techniques. As described hereinbelow, the feasibility of using colloidal micro- or nanogels as bio-inks is demonstrated. In addition, the effect of varying bio-ink concentration on the printing outcomes is described.

In some embodiments, one or more bio-ink compositions comprising colloidal micro- and/or nanogels can be printed, such as though the use of an ultrasonic 3D printing technique, to prepare a micro- and/or nanogel film and/or 3D scaffold for use in modular tissue engineering. The presently disclosed bio-inks and related methods provide many advantages, including precise control over cell adhesion and spreading, the ability to create defined scaffolds, the ability to customize bio-ink size, mechanics, and functionality, and the ability to provide improved bioactive properties. The presently disclosed compositions and methods can be used for a wide variety of applications, such as, but not limited to, bandages and other wound dressings, drug delivery, research use, and spinal cord injury.

In some embodiments, the presently disclosed subject matter provides a bio-ink composition comprising: (a) a bio-compatible micro- or nanogel; and a liquid carrier. In some embodiments, to enhance the printability of the bio-ink, the composition can further comprise (c) a viscosity control agent and/or (d) a surface tension control agent.

Typically, the bio-compatible micro- or nanogel is a colloidal micro- or nanogel that comprises a suspension of micro- and/or nanoparticles wherein the micro- and/or nanoparticles comprise a bio-compatible hydrophilic polymer. Suitable bio-compatible hydrophilic polymers include, but are not limited to, naturally derived polymers, such as fibrin, gelatin, hyaluronic acid, and cellulose, as well as synthetic polymers such as poly(alkylene glycols) (e.g., poly(ethylene glycol) and polyacrylamides, such as polyacrylamides comprising poly(N-isopropylacrylamide) (poly-NIPam)), as well as combinations of any of these. In some embodiments, the polymer comprises a poly-NIPam polymer.

In exemplary embodiments, the presently disclosed bio-ink can be prepared from a copolymer prepared by the free radical/precipitation polymerization of N-isopropylacrylamide (NIPam) with a synthetically compatible monomer (e.g., another vinyl monomer) comprising a functional side chain (e.g., a side chain comprising a chemically reactive group, such as a carboxylic acid, thiol, hydroxyl, amino, etc.) and/or a crosslinking agent. In some embodiments, the copolymer is prepared by the copolymerization of NIPam, acrylic acid (AAc), and a crosslinking agent, such as N,N-methylenebisacrylamide (BIS) and/or cystamine bisacrylamide. In some embodiments, the monomeric content of the polymer comprises between about 40% and about 100% NIPam, between 0% and about 30% AAc, and between about 0% and about 30% BIS. In some embodiments, the monomeric content of the polymer is at least about 50, 60, 70, 75, or 80% NIPam. In some embodiments, the monomeric content of the polymer comprises between about 1% and about 10% BIS (e.g., 1, 2, 3, 4, 5, 6, 7, 8, 9, or 10% BIS). In some embodiments, the monomeric content comprises 4% BIS. In some embodiments, the monomeric content of the polymer (i.e., the percentage of monomeric units derived from particular monomers as compared to the total number of all the monomeric units present in the polymer) comprises about 90% or 91% NIPam. In some embodiments, the polymer further comprises about 5% AAc, and about 4% BIS. Varying the amount of BIS or other crosslinking agent can change the mechanical properties of the micro- or nanogels and the films prepared therefrom. Varying the amount of AAc can change the charge of the micro- or nanogels and the films prepared therefrom, as well as the number of functional groups available for further modification.

The bio-ink composition can comprise any suitable concentration of the micro- or nanogel. In some embodiments, the bio-ink composition can comprise between about 0.1 mg/ml and about 100 mg/ml of the micro- or nanogel. In some embodiments, the composition comprises between about 0.2 mg/ml and about 20 mg/ml (e.g., about 0.2, 0.4, 0.6, 0.8, 1, 2, 3, 4, 5, 6, 7, 8, 9, 10, 11, 12, 13, 14, 15, 16, 17, 18, 19, or about 20 mg/ml) of the gel. In some embodiments, the composition comprises between about 0.2 and about 2 mg/ml. In some embodiments, the bio-ink composition comprises about 2 mg/ml of the bio-compatible micro- or nanogel.

The size of the particles in the micro- or nanogel can be controlled by varying the composition of the gel polymer and/or the synthesis conditions used to prepare the polymer. In some embodiments, the particles of the bio-compatible micro- or nanogel have an average swollen particle diameter of between about 100 nm and about 10 microns (e.g., 100, 200, 300, 400, 500, 600, 700, 800, 900, 1000, 1250, 1500, 1750 or 10000 nm). In some embodiments, the average swollen particle diameter is between about 500 nm and about 700 nm.

In some embodiments, the size of the particles can be dependent upon temperature. For example, when the gel comprises poly(NIPam), the particles are typically swollen when in an aqueous solution at room temperature, but can undergo a reversible phase transition at a higher temperature (e.g., at about 32° C. or at about body temperature) and expel a majority (e.g., about 90%) of the liquid contained in the swollen particles. Thus, in some embodiments, the expulsion of the liquid content of the gel at body temperature can be used to deliver drugs or cell growth agents contained in the liquid to targeted sites in a subject (e.g., a human or other mammalian subject).

To facilitate printing of the bio-ink (e.g., to keep the bio-ink from drying and clogging in a print-head and/or to increase the wicking of the ink to a print surface from the print-head), one or more viscosity control agents can be included in the bio-ink formulation. Any suitable viscosity control agent can be used. In some embodiments, a viscosity control agent can be selected that is biocompatible and/or that can be removed from a printed film or other assembly prepared from the bio-ink prior to its contact with a subject. For example, in some embodiments, the viscosity control agent can be removed by a washing step (e.g., an aqueous or aqueous buffer washing step) following the printing of the bio-ink. Alternatively, the viscosity control agent can be removed using an organic solvent or solvents, via evaporation, or via sublimation. In some embodiments, the viscosity control agent can be crosslinked into the printed material.

In some embodiments, the viscosity control agent comprises one or more agent selected from the group including, but not limited to, a polyalkylene glycol (e.g., a poly (ethylene glycol) (PEG) or poly(propylene glycol)), a polysaccharide, agarose, methylstyrene, amylopectin, butanediol, calcium stearate, glucosaminoglycan, glycerol, albumin, collagen, laminin, fibronectin, and elastin, as well as copolymers of any of the polymer (e.g., synthetic polymer) viscosity control agent materials. In some embodiments, the viscosity control agent is a PEG. The PEG or other polymeric viscosity control agent can have any suitable molecular weight. In some embodiments, the PEG has a weight average molecular weight ($M_w$) between about 100 Da and about 8,000 kDa. In some embodiments, the PEG has a $M_w$ between about 100 Da and about 5,000 Da. In some embodiments, the PEG has a $M_w$ between about 100 Da and about 1,000 Da (e.g., 100, 200, 300, 400, 500, 600, 700, 800, 900, or about 1,000 Da). In some embodiments the PEG is $PEG_{400}$.

In some embodiments, the bio-ink comprises up to about 50 vol % of the viscosity control agent (e.g., the PEG). In some embodiments, the bio-ink composition comprises at least about 5 vol % viscosity control agent (e.g., PEG) (e.g., 5, 10, 15, 20, 25, 30, 35, 40, 45, or about 50 vol %) viscosity control agent (e.g., the PEG). In some embodiments, the bio-ink composition comprises up to about 30 vol % viscosity control agent (e.g., PEG). In some embodiments, the bio-ink composition comprises between about 10 vol % and about 20 vol % viscosity control agent (e.g., PEG) (e.g., about 10, 11, 12, 13, 14, 15, 16, 17, 18, 19, or 20 vol % viscosity control agent (e.g., PEG)).

Any suitable surface tension agent can be used to facilitate the printing of the bio-ink. For example, the surface tension agent can be used to tailor the wetting properties of the bio-ink for printing on different substrates or surfaces. As with the viscosity control agent, in some embodiments, the viscosity control agent is selected so that it is biocompatible and/or can be removed from a printed film or other assembly prepared from the bio-ink prior to the end use of the film or assembly. Suitable surface tension agents can be selected from the group including, but not limited to, a surfactant, such as sodium dodecyl sulfate (SDS), hexamethyldisilazane (HMS), [7-hydroxy-9H-(1,3-dichloro-9,9-dimethyl-acridin-2-one)] (DDAO), or a sorbitan ester (e.g., TWEEN®), and an ionic liquid, such as, for example, 1,3-dimethylimidazolium methylsulphate, 1-hexyloxymethyl-3-methyl imidazolium bis(trifluoromethyl sulphonyl) imide, or didecyldimethylammonium nitrate. In some embodiments, the bio-ink can comprise between about 0.1 and about 100 mM of one or more surface tension agent (e.g., about 0.1, 0.2, 0.3, 0.4, 0.5, 1, 2, 5, 10, 15, 20, 25, 30, 35, 40, 45, 50, 60, 70, 80, 90 or about 100 mM of one or more surface tension agent).

Any suitable liquid carrier can be used. In some embodiments, the liquid carrier is an aqueous liquid. In some embodiments, the liquid carrier is water (e.g., deionized water) or saline. In some embodiments, the liquid carrier can comprise an aqueous buffer, such as, but not limited to, phosphate buffered saline (PBS). In some embodiments, the liquid carrier can be a cell culture media. In some embodiments, one or more additives can also be included in the bio-ink, such as, but not limited to, a metabolite, a growth factor, a cytokine, a chemokine, a CD antigen, neurotrophin, a hormone, an enzyme, a viral antigen, a bacterial antigen, a recombinant protein, a natural protein, a monoclonal antibody, a polyclonal antibody, a donor blood serum protein, a donor blood plasma protein, an antimicrobial agent, a small molecule drug, a cell, and combinations thereof. Exemplary growth factors include, but are not limited to, KGF, PDGF, $TGF_\beta$, interleukin, activin, colony stimulating factor, CTGF, EGF, Epigen, erythropoietin, FGF, galectin, HDGF, hepatocyte growth factor, IGFBP, insulin like growth factor, insulin, leptin, macrophage migration inhibitory factor, melanoma inhibitory factor, myostatin, noggin, NOV, omentin, oncostatin M, osteopontin, OPG, periostin, placenta growth factor, placental lactogen, prolactin, RANK ligand, retinol binding protein, stem cell factor, transforming growth factor, and VEGF. In some embodiments, the one or more additives include KGF, IL-2, and/or IL-6.

Suitable anti-microbial agents include anti-bacterial agents, anti-mycobacterial agents, anti-viral agents, anti-fungal agents, and anti-parasite agents. Suitable antimicrobials include antibiotics, analgesics, antimicrobial peptides and metallic compounds. Suitable analgesics include opioids, capsaicin, diclofenac, lidocaine, benzocaine, methyl salicylate, trolamine, prilocaine, pramoxine, dibucaine, phenol, tetracaine, camphor, dyclonine, and menthol. Suitable anti-inflammatories include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, and ibuprofen.

In some embodiments, the presently disclosed subject matter provides a three-dimensional (3D) material comprising one or more micro- or nanogel assemblies of one or more bio-ink compositions. Thus, the presently disclosed subject matter provides materials that comprise the printed bio-inks. In some embodiments, the micro- or nanogel assembly comprises or consists of a film, having a length and/or width that is substantially larger (e.g., at least 2, 3, 4, 5, 10, 15, 25, 50, or 100 times larger) than the thickness. In some embodiments, the 3D material comprises a combination of films/assemblies, which can have the same or different lengths, widths, and/or thicknesses. In some embodiments, the material can comprise a plurality of films/assemblies, wherein each film/assembly is prepared from a different bio-ink composition or combination of bio-ink compositions. Thus, in some embodiments, the material can comprise micro-gel or nanogel assemblies that have different mechanical properties (e.g., different hardness, viscoelasticity, elastic modulus, and/or loss tangent). In some embodiments, one or more mechanical properties of the 3D material and/or of an individual micro- or nanogel assembly of the 3D material can vary incrementally (e.g., in a step-wise manner) or continuously in one or more direction (i.e., in the x, y, and/or z direction). In some embodiments, one or more topological feature (e.g., the thickness) of the 3D material and/or of an individual micro- or nanogel assembly of the 3D material can vary incrementally or continuously in one or more direction. In some embodiments, the surface roughness of the 3D material and/or of an individual micro- or nanogel assembly of the 3D material can be varied.

In some embodiments, the 3D material further comprises one or more other components. For example, in some embodiments, one or more of the the one or more micro- or nanogel assemblies are in contact with (e.g., permanently or detachably affixed to) another material, such as, but not limited to, a substrate onto which the bio-ink was printed. In some embodiments, this material is selected from the group comprising, but not limited to, a cellulose-based material, a nanofiber-based material, a polyethylene vinyl acetate (PEVA) material, a polyester material, a polyurethane material, and a glass material. In some embodiments, the material is a material typically used for wound dressings or similar products, such as bandages, sutures, compresses, gauze wound packing materials, surgical drapes, other medical or veterinary wrappings, and the like. In some embodiments, the material is a material typically used for a surgical implant, e.g., a metal, a bio-compatible plastic, or a ceramic. For instance, the implant can be a stent, a joint replacement part, a screw for bone repair, an implantable drug delivery device, or an implantable device for organ monitoring and/or support. Thus, in some embodiments, the 3D material forms part of and/or is provided in the form of a bandage, a suture, a surgical implant, or a wound dressing. Such materials can also include other components, such as adhesives, water-proof backings, anti-microbial agents, etc.

In some embodiments, the presently disclosed subject matter provides a method of preparing a 3D biomaterial scaffold (e.g., a scaffold for supporting and/or directing cell adhesion and growth), wherein said biomaterial scaffold comprises a micro- or nanogel assembly. In some embodiments, the method comprises: (a) providing one or more bio-ink composition of the presently disclosed subject matter; and (b) printing the one or more bio-ink composition in a pre-determined pattern to form a printed layer.

Any suitable printing technique can be used (e.g., ink-jet printing, extrusion printing, etc.). In some embodiments, the printing comprises the use of a piezo-drop/ultrasound printing technique. Such techniques can be particularly useful for the presently disclosed subject matter in that they can be performed without the use of additional heat and/or mechanical forces that could damage the bio-ink components. In some embodiments, the printing comprises the use of a microplotter so that the bio-ink can be printed in one or more continuous line and/or arc patterns, as well as in a droplet-by-droplet manner. In some embodiments, the microplotter is an ultrasonic microplotter. In some embodiments, the printing comprises printing the one or more bio-ink composition from a glass capillary write-head (i) droplet-by-droplet and/or (ii) in a continuous line or arc. In some embodiments, the glass capillary write-head has a tip diameter between about 5 microns and about 30 microns (e.g., about 5, 10, 15, 20, 25, or 30 microns).

In some embodiments, the one or more bio-ink compositions are printed in a pre-determined pattern on a bio-compatible substrate or on a sacrificial substrate. For example, in some embodiments, the bio-ink can be printed directly onto a substrate that forms part of an end product comprising a micro- or nanogel assembly, such as a bandage, other wound dressing, or implant. Thus, in some embodiments, the substrate can comprise a cellulose-based material, a nanofiber-based material, a polyethylene vinyl acetate material, a polyester material, and/or a polyurethane material. In some embodiments, the substrate can be a metal or ceramic. The substrate can be a woven or non-woven material. In some embodiments, e.g., when the end product 3D material is intended as a stand-alone micro- or nanogel assembly or combination of assemblies, the substrate can be a sacrificial substrate which is removed after printing or after cells are cultured in the presence of the assembly or assemblies. Thus, a sacrificial substrate is a substrate that is not intended for use in a product that comes in contact with, or, more particularly, is implanted in, a living subject. In some embodiments, the sacrificial substrate is glass or another material comprising silica. In some embodiments, the substrate is a chemically cleaned glass or a glass coated with a coating agent.

Any suitable coating agent and/or concentration of coating agent can be used, e.g., to alter the surface properties of the substrate to control the contact angle of the ink on the substrate surface. For example, in some embodiments, the coating agent can make the surface of the substrate more hydrophobic in order to reduce spreading of the bio-ink on the surface. In some embodiments, the coating agent can make the surface of the substrate charged in order to enhance or reduce interaction of the surface with the bio-ink. In some embodiments, the coating agent can be an amino or polyamine. In some embodiments, the surface coating agent is selected from the group comprising polyethylenimine (PEI), bovine serum albumin (BSA), and (3-aminopropyl) trimethoxysilane (APTMS). In some embodiments, the sacrificial substrate is glass coated with PEI.

In some embodiments, the printing comprises printing a single layer of a bio-ink composition or compositions. In some embodiments, the concentration and/or chemical composition of the bio-ink is changed (incrementally or continuously) during the printing of the single layer, e.g., so that the printed layer includes a mechanical or topological gradient. Stated another way, in some embodiments, micro- or nanogels of different compositions or dilutions of micro- or nanogels of the same composition can be printed. For example, in some embodiments, the composition of the bio-ink is varied during the printing such that the particle size, the level of cross-linking, the amount of functional side chain monomer, and/or the amount of NIPam in the micro- or nanogel is varied. In some embodiments, the viscosity and/or surface tension of the bio-ink is varied during the printing. In some embodiments, the rate and/or frequency of the ultrasonic printing is varied to control the bio-ink density and/or printing resolution.

In some embodiments, the method further comprises printing the one or more bio-ink composition in a second pre-determined pattern to form a second printed layer. The second pre-determined pattern can be the same or different than the first pre-determined pattern. The second printed layer can be printed partially or completely onto the first printed layer. In some embodiments, the second printed layer is at least partially in contact with the first printed layer. Alternatively, the second printed layer can be printed on a sacrificial substrate and placed in contact with the first printed layer after printing. In some embodiments, one or more additional layers can be printed in one or more additional predetermined patterns, thus forming one or more additional printed layers. In some embodiments, each additional printed layer is at least partially in contact with a previously printed layer. Alternatively, each additional printed layer can be printed onto a sacrificial substrate and assembled into a combination of printed layers after printing.

In some embodiments, the presently disclosed subject matter provides a 3D biomaterial scaffold prepared according to a presently disclosed method. The scaffold can comprise one or more micro- or nanogel assembly prepared via a 3D printing technique. In some embodiments, the scaffold has one or more features having a length and/or width of less than about 50 nm. In some embodiments, the scaffold has one or more features having a length and/or width of between about 5 nm and about 30 nm (e.g., about 5, 10, 15, 20, 25, or about 30 nm). In some embodiments, the scaffold has one or more features having a length and/or width of between about 5 nm and about 10 nm (e.g., about 5, 6, 7, 8, 9, or 10 nm).

In some embodiments, the scaffold has a layer height of between about 50 nm and about 2 μm (e.g., about 50, 100, 200, 300, 400, 500, 600, 700, 800, 900, 1000, 1250, 1500, 1750, or about 2000 nm). In some embodiments, the layer height is about 400 nm. In some embodiments, the layer height is variable, e.g., in a continuous or non-continuous manner. In some embodiments, the scaffold comprises two or more layers of printed material. The layers can have the same or different dimensions and thus be partially or completely overlapping.

In some embodiments, the scaffold comprises a mechanical or topological gradient. For example, the scaffold can vary in chemical composition (e.g., in particle size or polymer composition) in one or more x, y, or z direction, thereby varying in one or more mechanical property. The gradient can be shallow or steep. In some embodiments, mechanical properties can vary by about 10 Pa/mm of printed area for a shallow mechanical gradient. In some embodiments, mechanical properties can vary by about 1000 Pa/mm of printed area for a steep mechanical gradient. In some embodiments, the height could vary from about 5 nm to about 5 microns while the length could vary from about 100 nm to about 20 microns to provide a shallow or steep topological gradient.

In some embodiments, the presently disclosed subject matter provides a method of preparing a biological tissue. In some embodiments, the method comprises: (a) providing one or more 3D biomaterial scaffolds of the presently disclosed subject matter; and (b) contacting the one or more scaffolds with a composition comprising one or more types of biological cells. For example, the one or more types of cells can comprise dermal fibroblasts. In one exemplary embodiment, the cells can comprise neonatal human dermal fibroblasts (nHDF), e.g., for the use of the presently disclosed scaffolds in promoting and directing cell proliferation. In some embodiments, the use of less crosslinked particles (i.e., particles with lower crosslinking density) results in less cell adhesion and slower cell migration. In some embodiments, the monomeric content of a crosslinker (e.g., BIS) is used to express the level of crosslinking density in the particles.

In some embodiments, the composition is an ex vivo sample comprising one or more types of cells and the method further comprises culturing the cells while they remain in contact with the one or more scaffolds. Suitable cell culture conditions, such as those that would be understood by one of ordinary skill in the art, can be used. Thus, in some embodiments, the biological tissue is prepared ex vivo, e.g., where the scaffolds are present on a suitable sacrificial substrate, such as, but not limited to a glass or coated glass substrate. In some embodiments, the ex vivo grown biological tissue is removed from the substrate and transferred to a subject, e.g., a human or other mammalian subject, in need of tissue replacement or regeneration. For example, the subject can be a subject who is undergoing surgery or who has otherwise suffered a wound. In some embodiments, a plurality of ex vivo grown biological tissues can be combined into a single tissue assembly.

In some embodiments, the subject of the presently disclosed methods is a human subject, although it is to be understood that the methods described herein are effective with respect to all animals, particularly warm-blooded animals, such as birds and mammals.

More particularly, provided herein is the treatment of mammals, such as humans, as well as those mammals of importance due to being endangered (such as Siberian tigers), of economic importance (animals raised on farms for consumption or another use (e.g., the production of wool) by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, such as chickens, ducks, geese, and other birds kept as livestock; wild birds, particularly birds that are endangered (e.g., bald eagles, California condors, etc.), and birds kept in zoos or as pets, e.g., parrots, cockatiels, etc. Thus, embodiments of the methods described herein include the treatment of livestock and pets.

In some embodiments, the composition comprising one or more types of biological cells is an in vivo cell composition and step (b) comprises implanting the one or more scaffolds in a subject (or otherwise placing the scaffold or scaffolds in contact with a subject tissue), optionally a human subject, in need of tissue replacement and/or regeneration. The one or more scaffolds can be free of any substrate (e.g., "stand-alone" scaffolds) or can be attached to a suitable biocompatible substrate. For example, the scaffolds can be incorporated into a wound dressing material and placed in contact with an open wound to promote healing of the wound. In some embodiments, the scaffolds can be implanted at a subcutaneous site to promote tissue healing/regeneration in tissue farther away from the skin.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Microgel Bio-Ink Synthesis

Microgel particles were created using a precipitation-polymerization reaction. Briefly, poly(N-isopropylacrylamide) (poly-NIPam), N,N'-methylenebis(acrylamide) (BIS), and acrylic acid (AAc) were added to 95 ml of de-ionized water to create a final solution with a total monomer/crosslinker concentration of 140 mM. The concentration of each constituent was calculated by taking a percentage of the final concentration of the solution, which, in this example, was 91% poly-NIPam, 4% BIS, and 5% AAc with 0.5 mM of sodium dodecyl sulfate (SDS) added to control for particle size. The solution was then filtered and added to a three-necked reaction vessel that had a nitrogen source, a condenser, and a thermometer attached to it. The solution was heated to 70° C. and allowed to reach thermal equilibrium for 1 hour all while under the flow of nitrogen gas and mixing at 450 revolutions per minute (RPM). Once thermal equilibrium was achieved, a 1 mM solution of ammonium persulfate (APS) was added to initiate the reaction. The reaction was allowed to proceed for 6 hours and cooled overnight while continuously stirring at 450 RPM. To remove any large microgel fragments, the cooled solution was filtered using glass wool. Dialysis was performed using 1000 kilodalton (kDa) tubing (Spectrum Laboratories, Inc., Rancho Dominguez, California, United States of America) to remove partially formed fragments. Water for dialysis was changed every 12-16 hours over the course of 48 hours. After 48 hours, the microgel solution was lyophilized and then reconstituted in water at a stock concentration of 5 mg/ml. Bio-inks were then created by diluting the stock concentration to either 2, 0.2, or 0.02 mg/ml and adding either 5%, 10%, or 20% low molecular weight polyethylene glycol (PEG) by volume.

Example 2

Surface Functionalization and Contact Angle Analysis

Glass slides were first cleaned in a sonicator for 15 minutes in each of the following solutions: anionic detergent (ALCONOXT™, Alconox, Inc., White Plains, New York, United States of America) diluted 3:100 in deionized water ($DiH_2O$), $DiH_2O$, acetone, absolute ethanol, and isopropyl alcohol. The glass slides were then washed twice with deionized water and dried with nitrogen. The dried glass slides were then functionalized with one of the following: (3-aminopropyl)triethoxysilane (APTMS), polyethylenimine (PEI), or bovine serum albumin (BSA). For APTMS functionalization, APTMS was diluted 1:100 into absolute ethanol. The clean glass slides were then covered with the diluted APTMS solution and shaken at room temperature for 2 hours. At the end of the 2 hours, the glass slides were washed twice with $DiH_2O$ and allowed to dry. For functionalization with PEI, PEI was first diluted to a concentration of 0.05 monomolar in $DiH_2O$. The clean glass slides were then covered with the PEI solution and incubated overnight at 4° C. Following the incubation, the slides were washed twice with $DiH_2O$ and allowed to dry. Finally, for BSA functionalization a solution of 1% BSA by weight was made into $DiH_2O$. The clean glass slides were allowed to incubate in the BSA solution overnight at 4° C. Following incubation, the slides were washed twice with $DiH_2O$ and allowed to dry.

Contact angle measurements were taken using a Ramé-Hart Advanced Contact Goniometer (Model 102; Ramé-Hart Instrument Co., Succasunna, New Jersey, United States of America). DropImage Advanced software (Ramé-Hart Instrument Co., Succasunna, New Jersey, United States of America) was used to image droplets on all of the functionalized glass slides mentioned above. In order to measure the contact angle, a line tangent to the corner of the liquid droplet is drawn and the angle that the tangent makes with the horizontal surface is measured. A contact angle is measured on each side of the droplet and averaged together to obtain the overall contact angle for the droplet. The solutions used to create a droplet on each of the functionalized surfaces are water and microgel solutions at either 2, 0.2, or 0.02 mg/ml with either 5%, 10%, or 20% PEG.

Figure 1B:
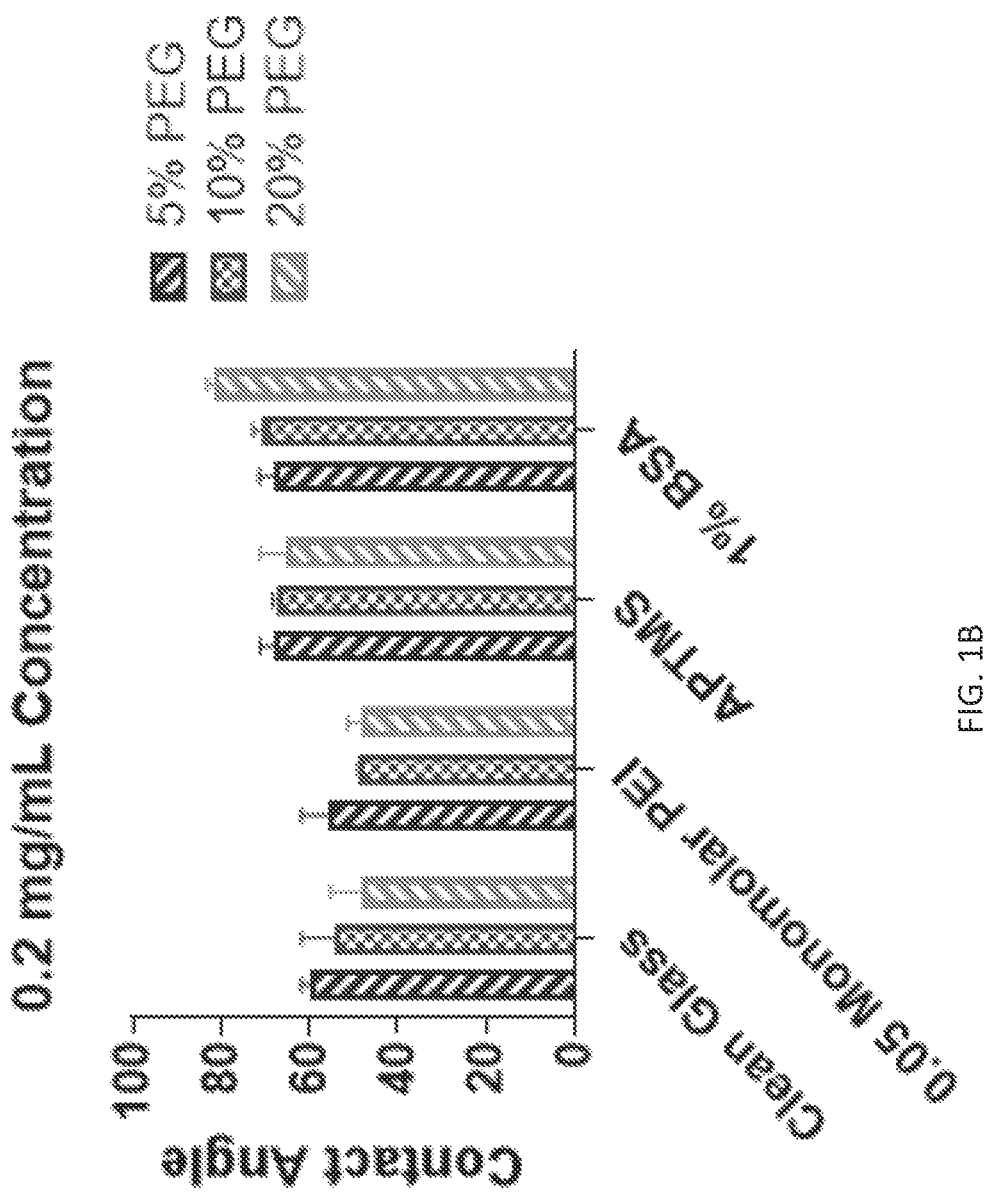
FIG. 1B is a graph showing the contact angle measurements of a microgel bio-ink comprising 0.2 milligrams per milliliter (mg/ml) of a poly(N-isopropylacrylamide) (poly-NIPam) microgel prepared using 4 percent (%) N,N'-methylenebis(acrylamide) (BIS) and further comprising varying amounts of polyethylene glycol (PEG) printed on surfaces with different coatings. The different surfaces are as described on the x-axis: clean glass, glass treated with 0.5 monomolar polyethylenimine (PEI), (3-aminopropyl)triethoxysilane (APTMS), or 1% bovine serum albumin (BSA). For each surface, results are shown (from left to right) for a bio-ink comprising 5% PEG (black diagonal striped bars), 10% PEG (checker board bars), or 20% PEG (grey diagonal striped bars).
Figure 1C:
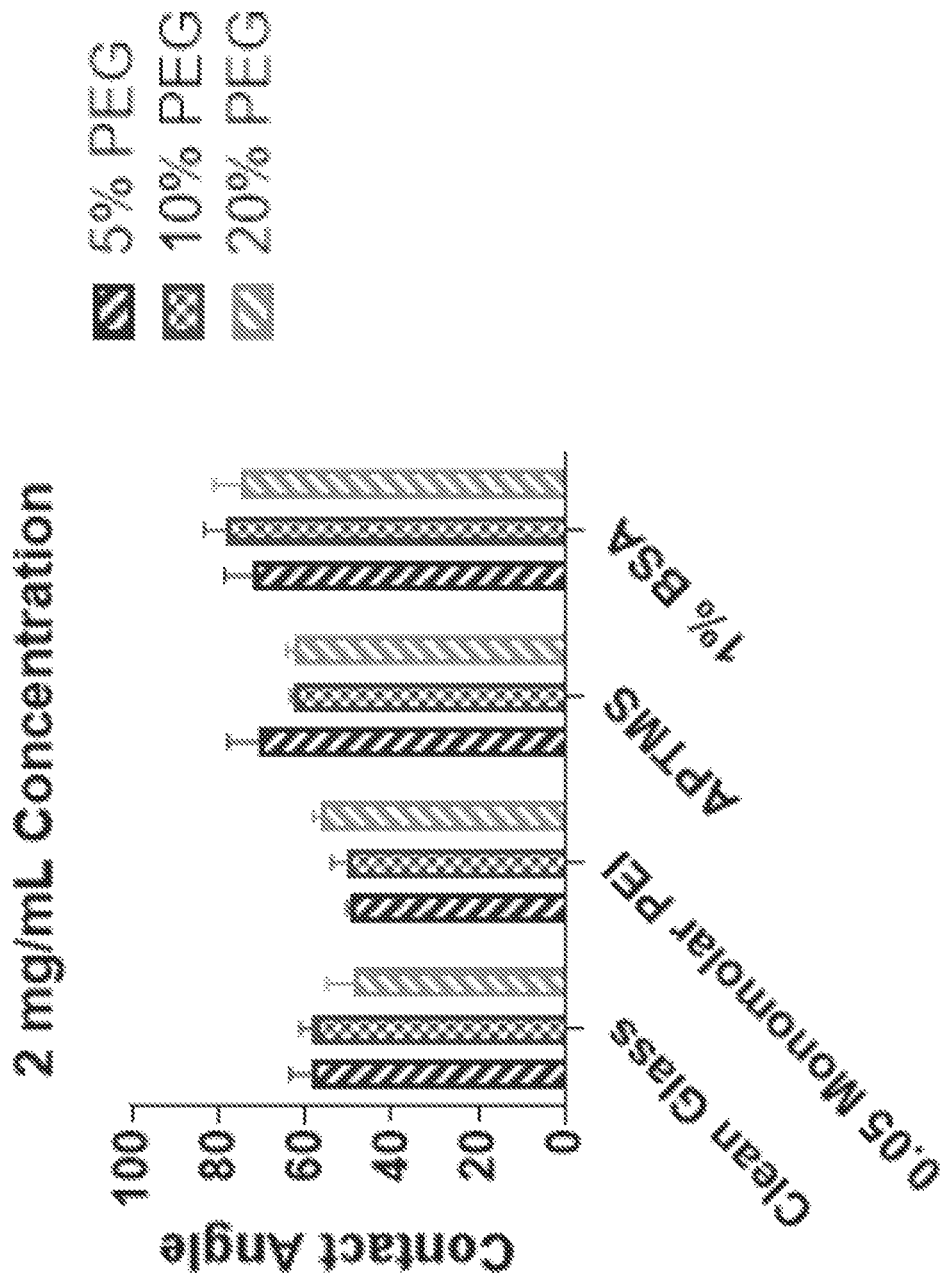
FIG. 1C is a graph showing the contact angle measurements of a microgel bio-ink comprising 2 milligrams per milliliter (mg/ml) of a poly(N-isopropylacrylamide) (poly-NIPam) microgel prepared using 4 percent (%) N,N-methylenebis(acrylamide) (BIS) and further comprising varying amounts of polyethylene glycol (PEG) printed on surfaces with different coatings. The different surfaces are as described on the x-axis: clean glass, glass treated with 0.5 monomolar polyethylenimine (PEI), (3-aminopropyl)triethoxysilane (APTMS), or 1% bovine serum albumin (BSA). For each surface, results are shown (from left to right) for a bio-ink comprising 5% PEG (black diagonal striped bars), 10% PEG (checker board bars), or 20% PEG (grey diagonal striped bars).

Discussion: All three of APTMS, PEI and BSA include amino groups that can be positively charged, providing potential electrostatic interaction with microgels, which tend to be negatively charged. The contact angles of microgel bio-inks comprising different PEG percentages and different microgel concentrations were measured on glass surfaces that were cleaned and either had no coating or a coating of 0.05 mM PEI, APTMS, or 1% BSA. See FIGS. 1A-1C. It was found that the contact angle of the bio-inks increased in the following order: plain glass, PEI, APTMS, and BSA, where plain glass had the lowest contact angle on average and BSA had the highest contact angle on average. It was also found that the contact angle remained fairly consistent among the different PEG concentrations and microgel concentrations, suggesting that the surface properties played a more dominant role in determining the contact angle of the bio-ink than did the amount of PEG or microgel present in the bio-ink.

Example 3

Bio-Ink Micro-Plotting

Figure 2A:
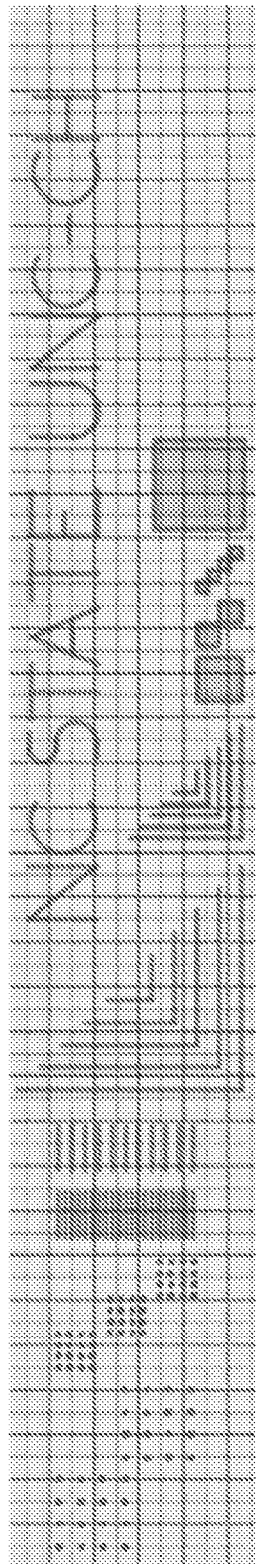
FIG. 2A is a schematic drawing of a printing pattern used to print microgel bio-inks of the presently disclosed subject matter.

Glass capillary print heads were created using glass capillary tubes (G-2 tubes; Narishige International USA, Inc., Amityville, New York, United States of America). Using a micropipette puller (PC-10 model; Narishege International USA, Inc., Amityville, New York, United States of America) and a microforge (MF-900 model; Narishege International USA, Inc., Amityville, New York, United States of America), the glass capillary tubes were pulled to the desired length and cut to have a diameter of 50 µm. The patterns used for printing all of the microgel bio-inks were designed using the SONODRAW™ GIX II software (SonoPlot, Inc., Middleton, Wisconsin, United States of America) and can be seen in FIG. 2A. The micropipette tips were then superglued onto a piezoelectric element and fit into the holder on a microplotter (SONOPLOT® GIX Microplotter II; SonoPlot, Inc., Middleton, Wisconsin, United States of America). The microplotter used is an ultrasonic droplet machine that uses controlled ultrasonic pumps to release fluid from the micropipette tips. The printing pattern created in the SONODRAW™ software was uploaded to the SonoPlot® printing software and the printing of the pattern commenced. The printer does not touch the surface of the material being printed on, thus providing for the printing of soft materials, such as hydrogels, without marking or damaging the surface. In addition, the printer is able to handle sensitive biomolecules without causing deactivation or shear while dispensing and while still maintaining a 20-micron positioning resolution. After printing, the glass slides were imaged using an EVOS® microscope (ThermoFisher Scientific Inc., Waltham, Massachusetts, United States of America) and the patterns were analyzed in ImageJ in order to measure the printed dots radii and circularity as well as the length and thickness of the lines printed and the percentage of the overall line printed.

Discussion: A pattern was created in order to showcase the wide array of parameters possible using a piezoelectric printing technique. Dots, lines, curves, filled areas, and right angles were created at different length scales and at different resolutions in order to assess the viability of a microgel bio-ink to be used in the fabrication of a complex material scaffold. See FIG. 2A. This pattern was then used for all subsequent printing.

Figure 2B:
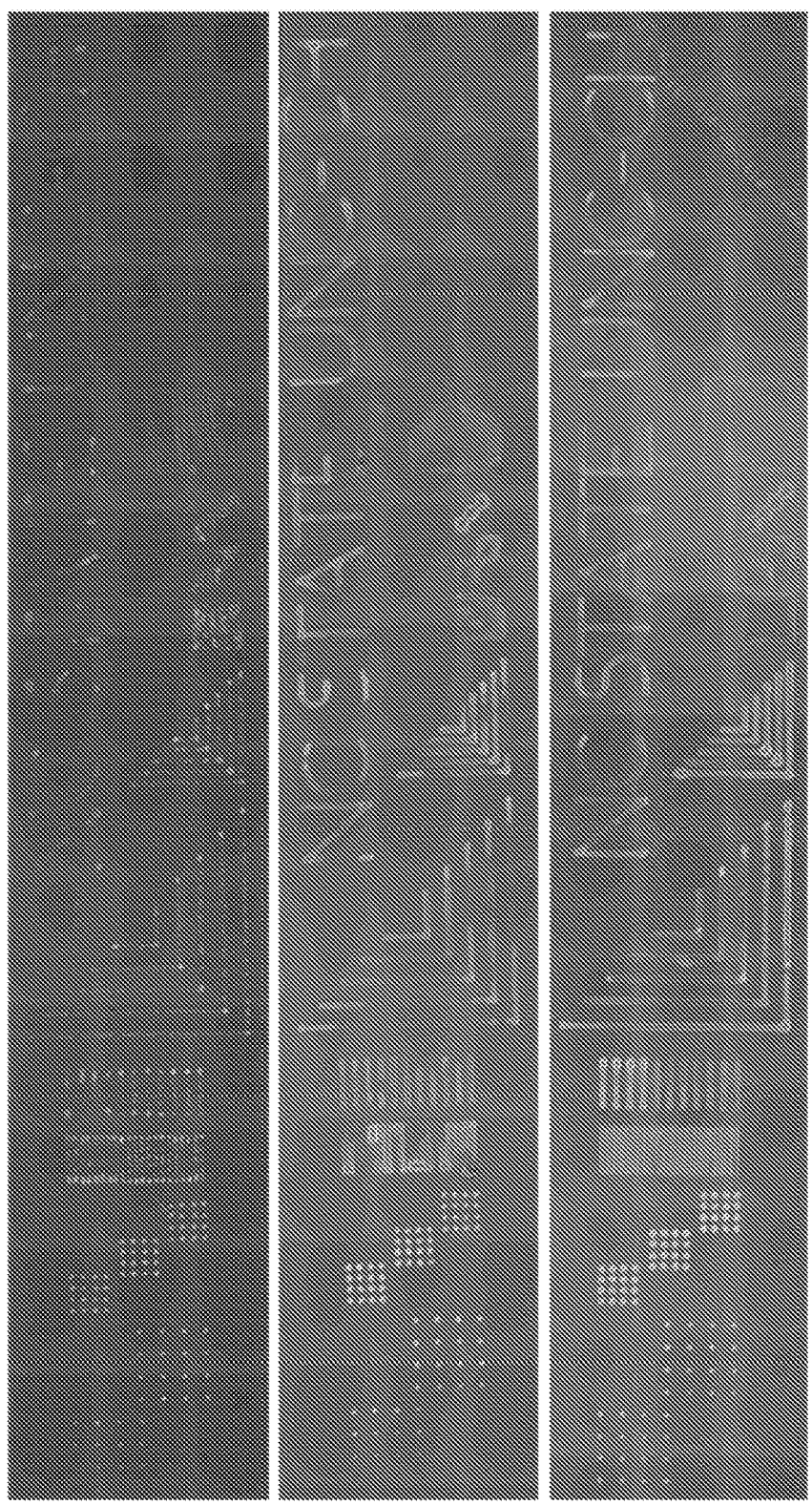
FIG. 2B is a series of scanning electron microscopy (SEM) images of microgel bio-inks of the presently disclosed subject matter printed on a clean glass slide using glass capillary needles with 50 micrometer (μm) diameters according to the pattern shown in FIG. 2A. The top panel is an SEM image of the pattern printed using a microgel bio-ink comprising 0.02 milligrams per milliliter (mg/ml) of a poly(N-isopropylacrylamide) (poly-NIPam) microgel prepared using 4 percent (%) N,N-methylenebis(acrylamide) (BIS) and further comprising 20% polyethylene glycol (PEG). The middle panel is an SEM image of a pattern printed using a microgel bio-ink comprising 0.2 mg/ml of a poly(NIPam) microgel prepared using 4% BIS and further comprising 20% PEG. The bottom panel is an SEM image of a pattern printed using a microgel bio-ink comprising 2 mg/ml of a poly(NIPam) microgel prepared using 4% BIS and further comprising 20% PEG.
Figures 3A, 3B:
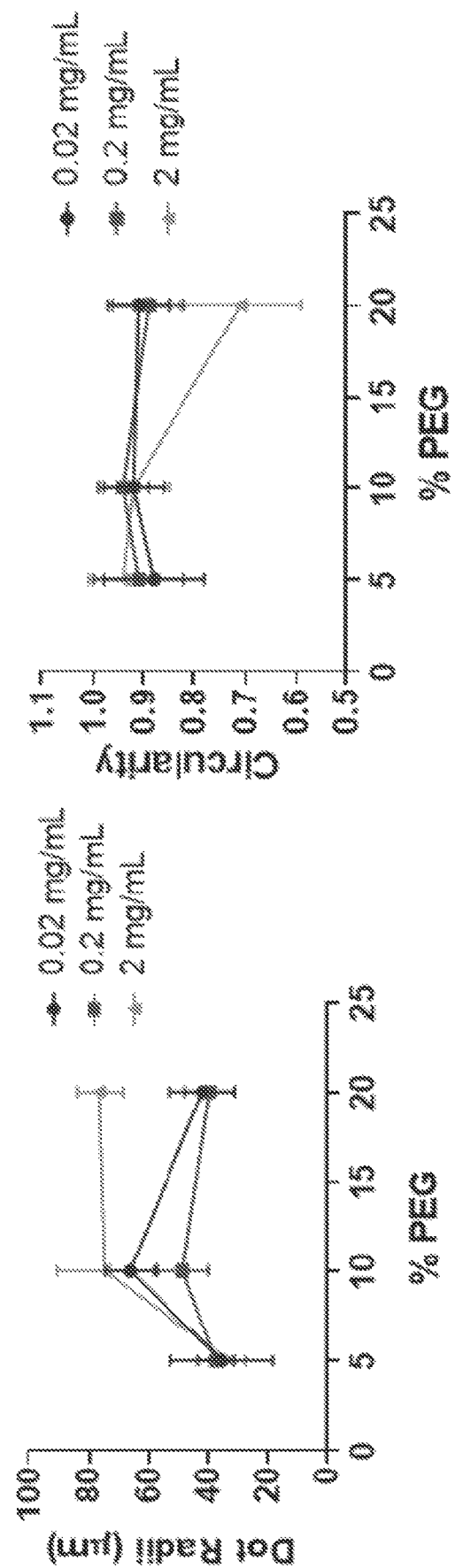
FIG. 3A is a graph showing the effect of bio-ink composition on dot radii (measured in microns (μm)) in patterns printed with microgel bio-inks of the presently disclosed subject matter. Data is provided for microgel bio-inks comprising 0.02 milligrams per milliliter (mg/ml) of a poly(N-isopropylacrylamide) (poly-NIPam) microgel prepared using 4 percent (%) N,N-methylenebis(acrylamide) (BIS) (circles), 0.2 mg/ml of a poly-NIPam microgel prepared using 4% BIS (squares), or 2 mg/ml of a poly-NIPam microgel prepared using 4% BIS (triangles). Polyethylene glycol (PEG) concentration in the bio-ink varied from 5% to 20% as indicated in the x-axis.
FIG. 3B is a graph showing the effect of bio-ink composition on dot circularity (measured as a fraction in comparison to a perfect circle having a value of 1.0) in patterns printed with microgel bio-inks of the presently disclosed subject matter. Data is provided for microgel bio-inks comprising 0.02 milligrams per milliliter (mg/ml) of a poly(N-isopropylacrylamide) (poly-NIPam) microgel prepared using 4 percent (%) N,N-methylenebis(acrylamide) (BIS) (circles), 0.2 mg/ml of a poly-NIPam microgel prepared using 4% BIS (squares), or 2 mg/ml of a poly-NIPam microgel prepared using 4% BIS (triangles). Polyethylene glycol (PEG) concentration in the bio-ink varied from 5% to 20% as indicated in the x-axis.
Figures 3C, 3D:
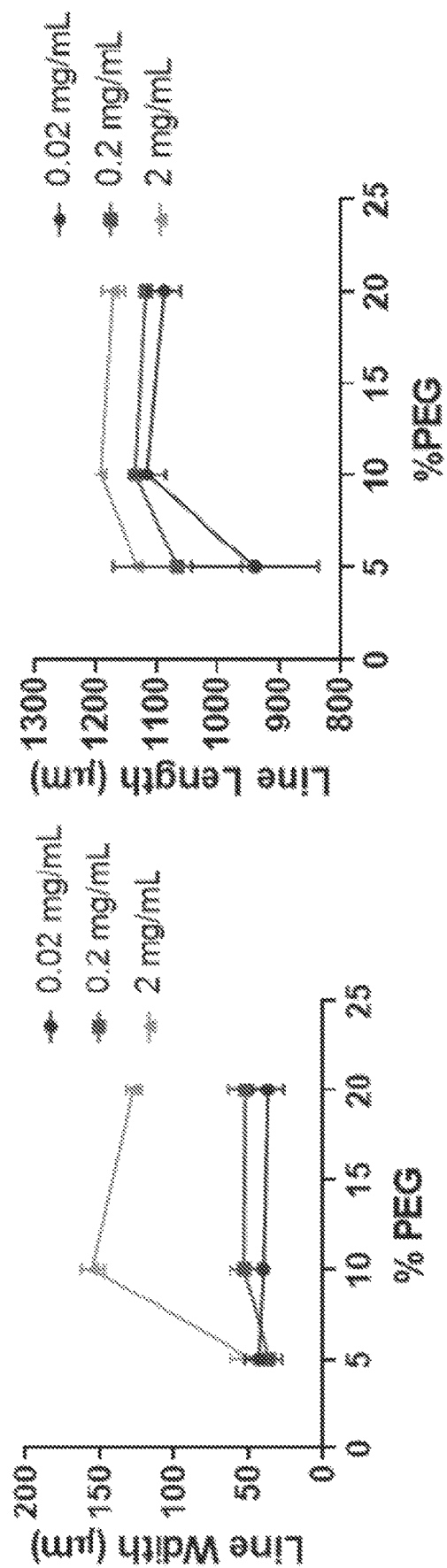
FIG. 3C is a graph showing the effect of bio-ink composition on printed line width (measured in microns (μm)) in patterns printed with microgel bio-inks of the presently disclosed subject matter. Data is provided for microgel bio-inks comprising 0.02 milligrams per milliliter (mg/ml) of a poly(N-isopropylacrylamide) (poly-NIPam) microgel prepared using 4 percent (%) N,N-metheylenebis(acrylamide) (BIS) (circles), 0.2 mg/ml of a poly-NIPam microgel prepared using 4% BIS (squares), or 2 mg/ml of a poly-NIPam microgel prepared using 4% BIS (triangles). Polyethylene glycol (PEG) concentration in the bio-ink varied from 5% to 20% as indicated in the x-axis.
FIG. 3D is a graph showing the effect of bio-ink composition on printed line length (measured in microns (μm)) in patterns printed with microgel bio-inks of the presently disclosed subject matter. Data is provided for microgel bio-inks comprising 0.02 milligrams per milliliter (mg/l) of a poly(N-isopropylacrylamide) (poly-NIPam) microgel prepared using 4 percent (%) N,N-methylenebis(acrylamide) (BIS) (circles), 0.2 mg/ml of a poly-NIPam microgel prepared using 4% BIS (squares), or 2 mg/ml of a poly-NIPam microgel prepared using 4% BIS (triangles). Polyethylene glycol (PEG) concentration in the bio-ink varied from 5% to 20% as indicated in the x-axis.
Figure 3E:
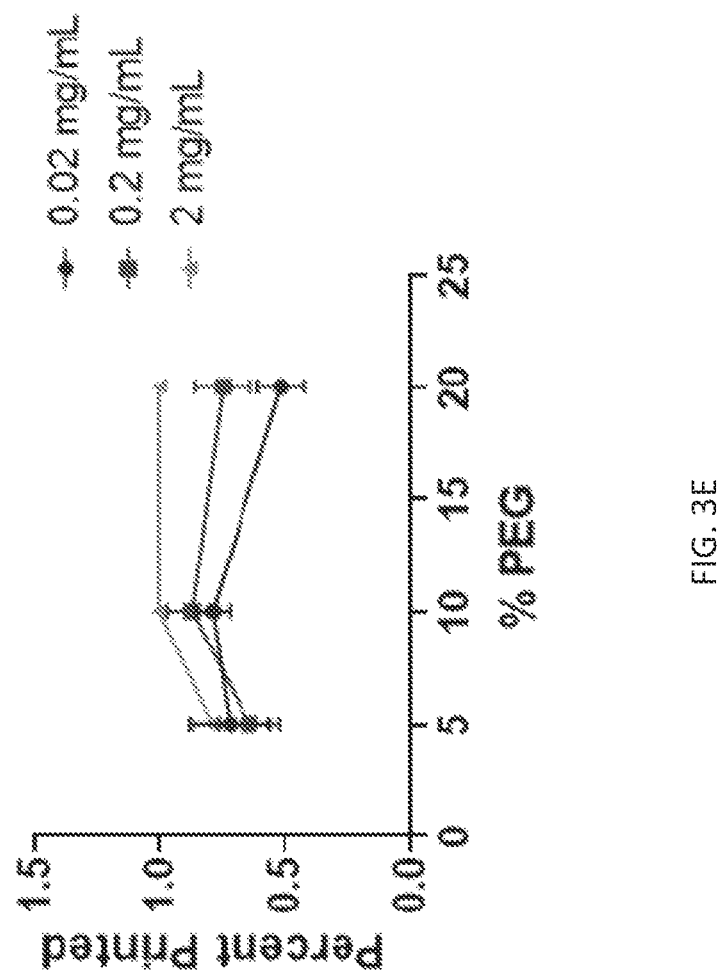
FIG. 3E is a graph showing the effect of bio-ink composition on percentage of a pattern printed (compared to a pattern that was 100 percent (%) printed, which was given the value of 1.0) with microgel bio-inks of the presently disclosed subject matter. Data is provided for microgel bio-inks comprising 0.02 milligrams per milliliter (mg/ml) of a poly(N-isopropylacrylamide) (poly-NIPam) microgel prepared using 4% N,N-methylenebis(acrylamide) (BIS) (circles), 0.2 mg/ml of a poly-NIPam microgel prepared using 4% BIS (squares), or 2 mg/ml of a poly-NIPam microgel prepared using 4% BIS (triangles). Polyethylene glycol (PEG) concentration in the bio-ink varied from 5% to 20% as indicated in the x-axis.
Figure 4B:
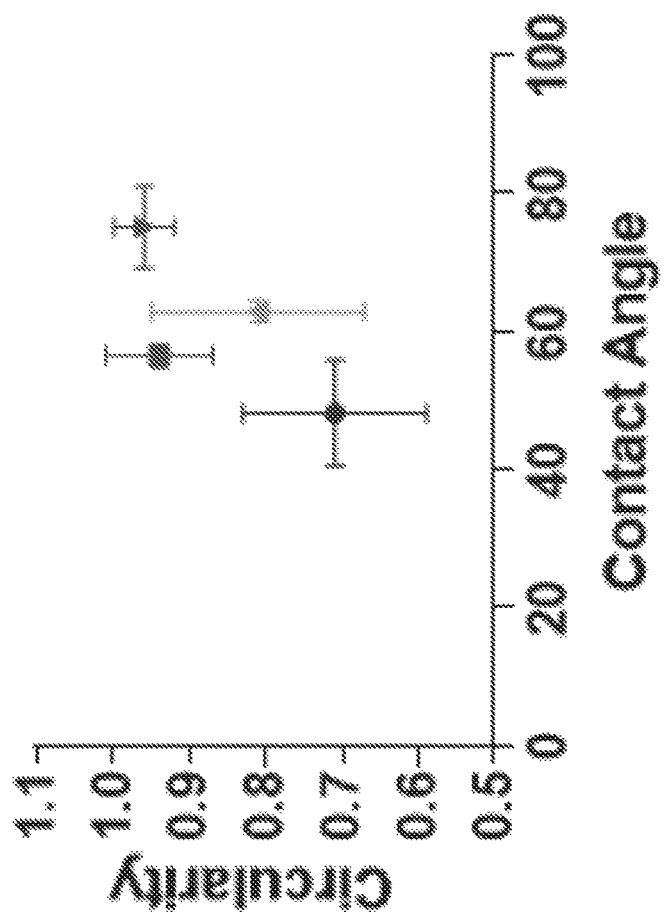
FIG. 4B is a graph showing the effect of surface coating and contact angle on dot circularity (presented as a fraction compared to a perfect circle having a value of 1.0) in patterns printed with a microgel bio-ink comprising 2 milligrams per milliliter (mg/ml) of a poly(N-isopropylacrylamide) (poly-NIPam) microgel prepared using 4 percent (%) N,N-methylenebis(acrylamide) (BIS) and further comprising 20% polyethylene glycol (PEG). Data is provided for bio-ink printed on clean glass (circle), 0.05 monomolar polyethylenimine (PEI; square), (3-aminopropyl)triethoxysilane (APTMS, upward-pointing triangle), or 1% bovine serum albumin (BSA, downward-pointing triangle).
Figure 4A:
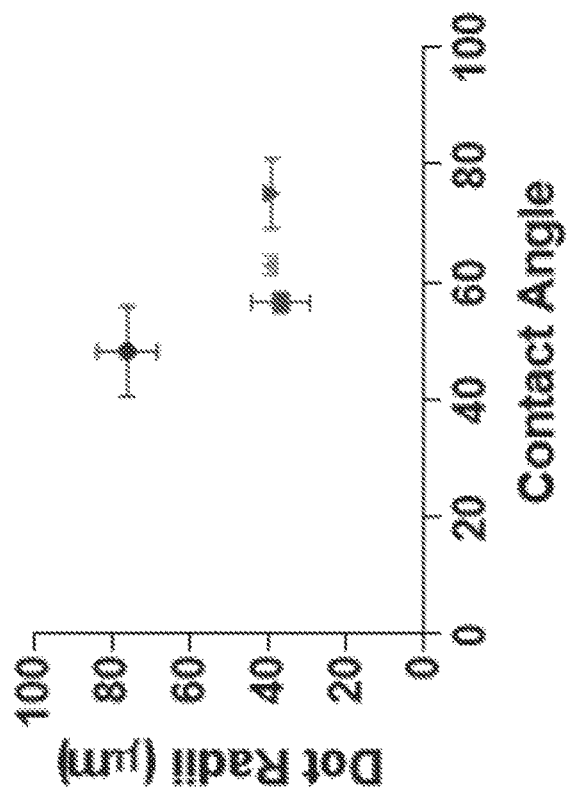
FIG. 4A is a graph showing the effect of surface coating and contact angle on dot radii (measured in microns (μm)) in patterns printed with a microgel bio-ink comprising 2 milligrams per milliliter (mg/ml) of a poly(N-isopropylacrylamide) (poly-NIPam) microgel prepared using 4 percent (%) N,N-methylenebis(acrylamide) (BIS) and further comprising 20% polyethylene glycol (PEG). Data is provided for bio-ink printed on clean glass (circle), 0.05 monomolar polyethylenimine (PH; square), (3-aminopropyl)triethoxysilane (APTMS, upward-pointing triangle), or 1% bovine serum albumin (BSA, downward-pointing triangle).
Figures 4C, 4D:
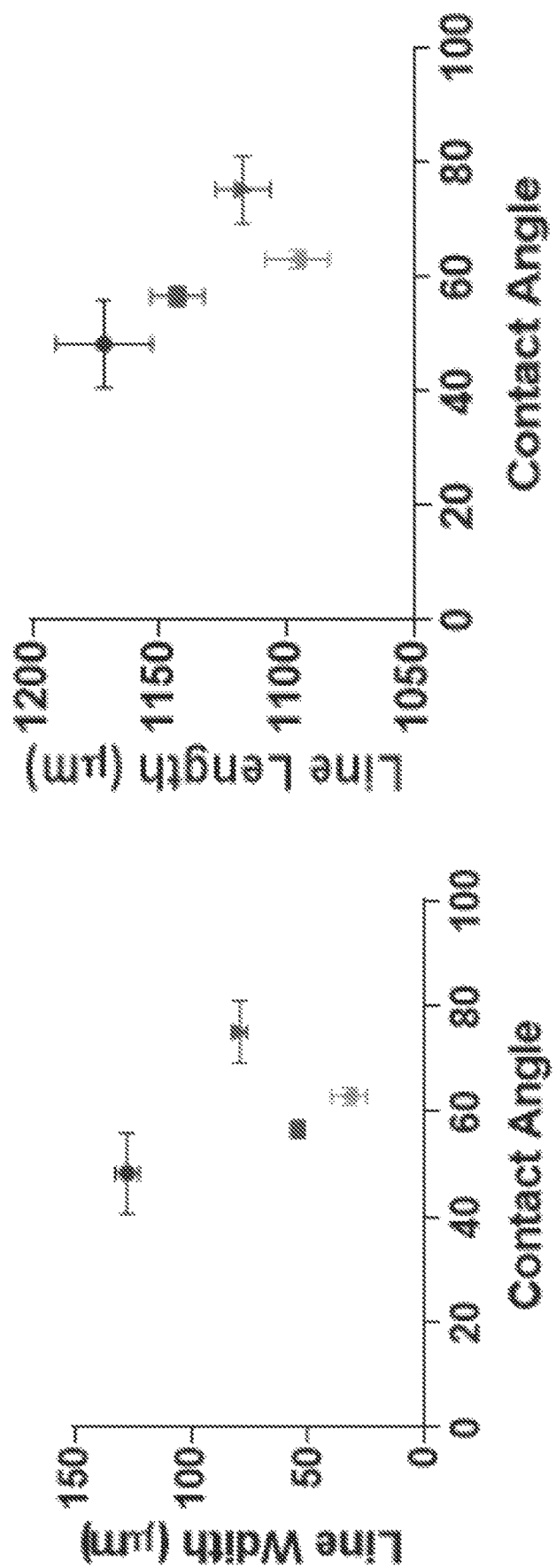
FIG. 4C is a graph showing the effect of surface coating and contact angle on line width (measured in micrometer (μm)) in patterns printed with a microgel bio-ink comprising 2 milligrams per milliliter (mg/ml) of a poly(N-isopropylacrylamide) (poly-NIPam) microgel prepared using 4 percent (%) N,N-methylenebis(acrylamide) (BIS) and further comprising 20% polyethylene glycol (PEG). Data is provided for bio-ink printed on clean glass (circle), 0.05 monomolar polyethylenimine (PH; square), (3-aminopropyl)triethoxysilane (APTMS, upward-pointing triangle), or 1% bovine serum albumin (BSA, downward-pointing triangle).
FIG. 4D is a graph showing the effect of surface coating and contact angle on line length (measured in micrometer (μm)) in patterns printed with a microgel bio-ink comprising 2 milligrams per milliliter (mg/ml) of a poly(N-isopropylacrylamide) (poly-NIPam) microgel prepared using 4 percent (%) N,N-methylenebis(acrylamide) (BIS) and further comprising 20% polyethylene glycol (PEG). Data is provided for bio-ink printed on clean glass (circle), 0.05 monomolar polyethylenimine (PEI; square), (3-aminopropyl)triethoxysilane (APTMS, upward-pointing triangle), or 1% bovine serum albumin (BSA, downward-pointing triangle).
Figure 4E:
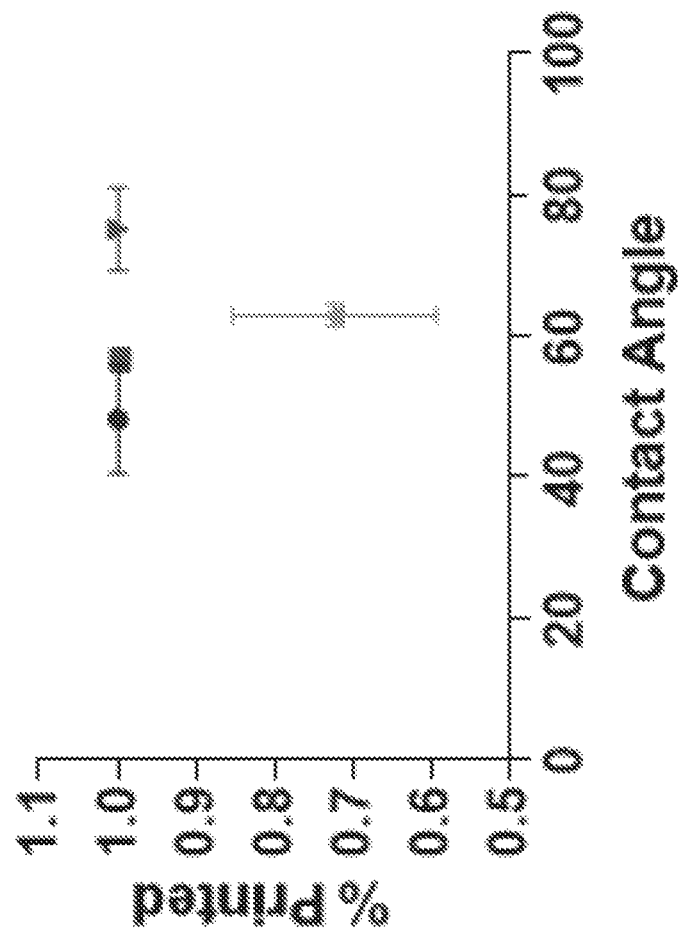
FIG. 4E is a graph showing the effect of surface coating and contact angle on the percentage (%) of pattern printed in patterns printed with a microgel bio-ink comprising 2 milligrams per milliliter (mg/ml) of a poly(N-isopropylacrylamide) (poly-NIPam) microgel prepared using 4% N,N-methylenebis(acrylamide) (BIS) and further comprising 20% polyethylene glycol (PEG). Data is provided for bio-ink printed on clean glass (circle), 0.05 monomolar polyethylenimine (PEI; square), (3-aminopropyl)triethoxysilane (APTMS, upward-pointing triangle), or 1% bovine serum albumin (BSA, downward-pointing triangle).

Microgel bio-inks were printed onto clean glass surfaces with either a concentration of 0.02 mg/ml, 0.2 mg/ml, or 2 mg/ml of microgel and 5%, 10%, or 20% PEG. The printed microgel bio-inks were allowed to dry before imaging on an EVOS microscope. Due to the size of the prints, an array of 4× images were taken and stitched together to create a final full image of the completed print. Exemplary prints of bio-inks at varying concentration of microgel and with 20% PEG are shown in FIG. 2B and are in keeping with the the results that were observed with other bio-ink formulations.

After being imaged on the EVOS microscope, the printed patterns were analyzed in ImageJ in order to calculate printed dot radii, printed dot circularity, printed line width, printed line length, and the average percent of the pattern printed. See FIGS. 3A-3E. Results show that as the concentration of microgel and the percentage of PEG increases, so does the size of the printed features, as well as the percentage of the template pattern that successfully printed.

Bio-inks with a microgel concentration of 2 mg/ml and 20% PEG were printed on glass surfaces with either PEI, APTMS, or BSA surface coatings. These prints were imaged on an EVOS microscope and the print features were analyzed in ImageJ to assess printed dot radii, printed dot circularity, printed line width, printed line length, and the average percent of the pattern printed. See FIGS. 4A-4E. Results showed that as contact angle increased, dot radii decreased, while dot circularity increased. However, when the printed lines were analyzed, a potential biphasic response was observed where line width and line length decreased as contact angle increased but then began to increase again after a contact angle of around 60 degrees. The APTMS printed surface was the only surface where less than 100% of the template pattern printed successfully. Without being bound to any one theory, it is possible that after a certain contact angle value is passed, other surface properties, such as surface charge magnitude and density, can influence printing parameters.

Summary: The results demonstrate that nanogel film construction is possible through 3D printing of nanogel bio-inks. The results indicate that microgel bio-ink formulations can be tuned to optimize the printed results and that different formulations can be used for different applications. For example, nanogel solution dilution results in less accumulation of nanogels in the prints. The 3D printing process can also be optimized to generate complex patterns of nanogel films which can provide for fine control over cell adhesion and cell spreading. Accordingly, 3D printing has potential for creating nanogel films with unique patterns and architecture, as compared to homogenous layer-by-layer deposition techniques.

Example 4

Cell Morphology and Migration in Microgel Films

Glass slides with printed bio-ink comprising varying amounts of crosslinking were sterilized with 70% ethanol for 20 minutes and then washed twice with phosphate buffered saline (PBS). Neonatal Human Dermal Fibroblasts (nHDF) cells were maintained at 37° C. in Dulbecco's Modified Eagle Medium (DMEM) supplemented with 10% fetal bovine serum (FBS) and antibiotics in a humidified atmosphere containing 5% $CO_2$. Cells were dissociated with PBS at 37° C. for 15 minutes. After centrifugation, cells were re-suspended and seeded on micro-patterned surfaces at a density of 50,000 cells per ml and were allowed to attach for 24 hours. The cells cultured on the prints were then fixed using the Image-iT Fix-Perm Kit (ThermoFisher Scientific, Waltham, Massachusetts, United States of America) according to the manufacturer's instructions. Fixed cells were stained (e.g., with a fluorescent actin stain) and imaged using fluorescent microscopy.

Figure 5A:
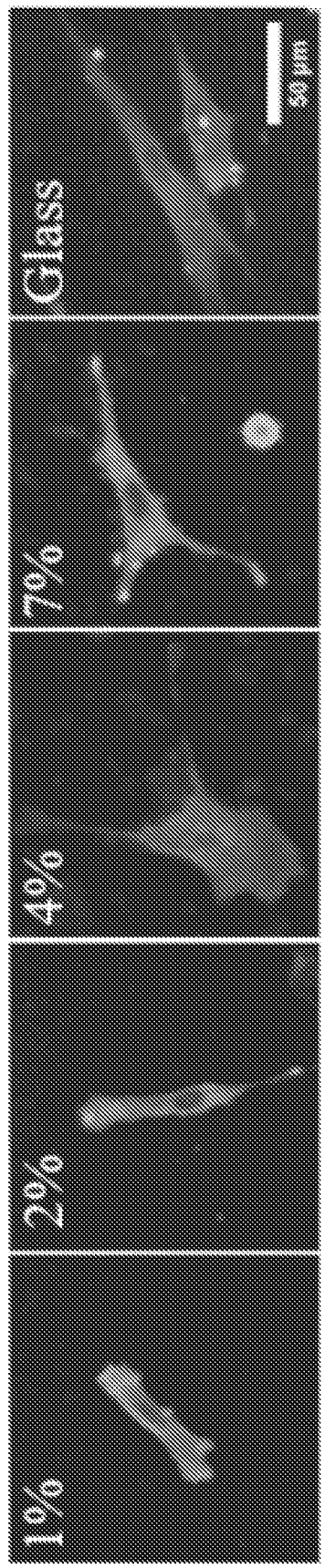
FIG. 5A is a series of fluorescent micrograph images of neonatal human dermal fibroblast (nHDF) cells cultured on printed microgel assemblies prepared from bio-inks of the presently disclosed subject matter having different internal crosslinking density. From left to right, the first four images show a microgel having 1 percent (%) internal crosslinking density, 2% internal crosslinking density, 4% internal crosslinking density, and 7% internal crosslinking density. The image on the far right shows nHDF cells cultured on a glass slide in the absence of a microgel prepared from a bio-ink of the presently disclosed subject matter. The scale bar in the lower right of the image on the far right represents 50 micrometers (μm).
Figure 5C:
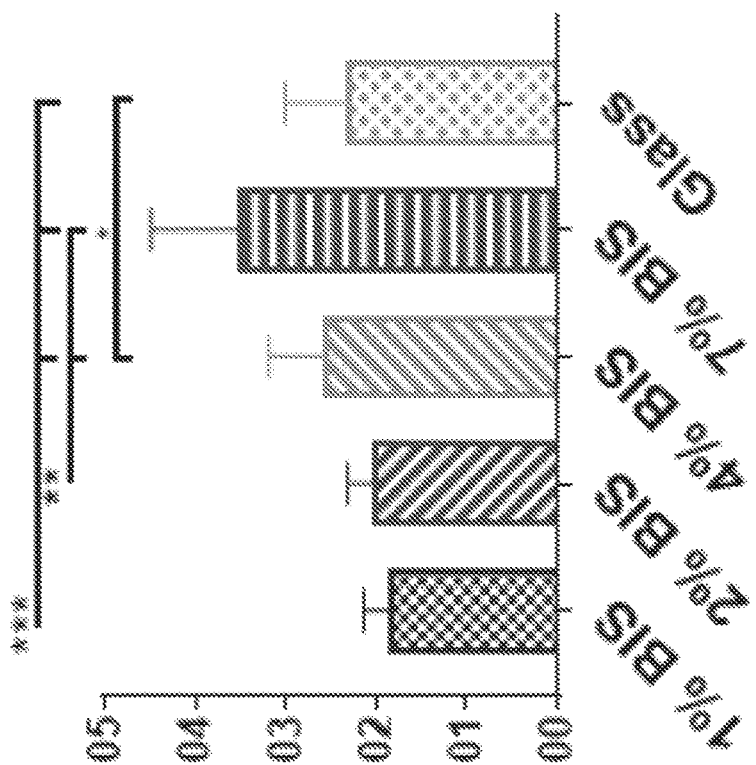
FIG. 5C is a graph showing the effect on cellular migration velocities (measured in micrometers per second (μm/sec)) for the cells cultured on the microgel films described in FIG. 5A. Data for the microgel with 1 percent (%) internal crosslinking density (1% N,N-methylenebis(acrylamide) (BIS)) is shown in the bar with the checker board pattern, data for the microgel with 2% internal crosslinking density (2% BIS) is shown in the bar with black diagonal stripes, data for the microgel with 4% internal crosslinking density (4% BIS) is shown in the bar with the grey diagonal stripes, data for the microgel with 7% internal crosslinking density (7% BIS) is shown in the bar with the horizontal stripes), and data for cells cultured on a glass slide in the absence of a microgel (Glass) is shown in the bar with the dots. *$p<0.05$, $p<0.005$, *$p<0.0005$
Figure 5B:
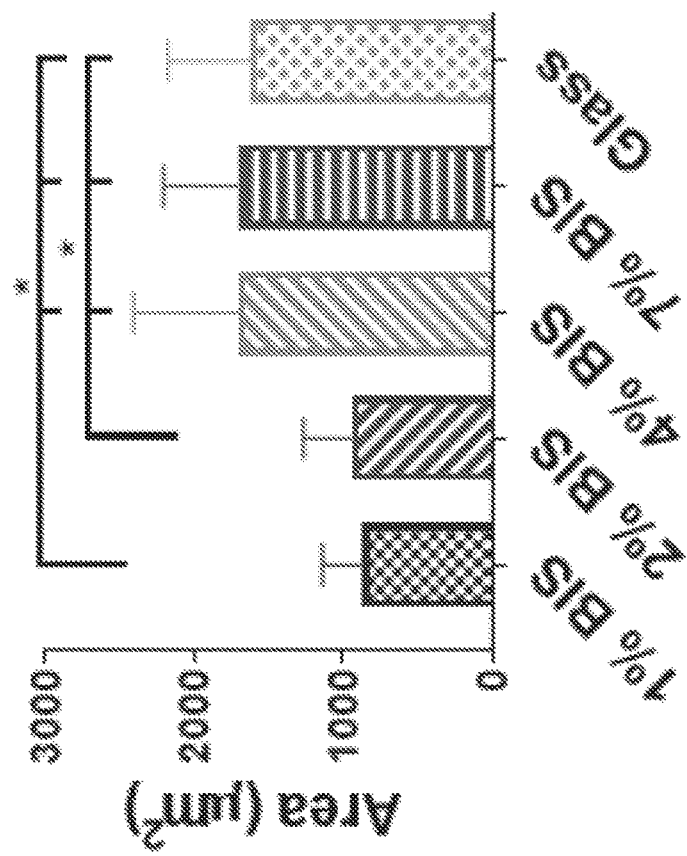
FIG. 5B is a graph showing the effect on cell area (measured in square micrometers ($\mu m^2$)) in the cells cultured on the microgel films described in FIG. 5A. Data for the microgel with 1 percent (%) internal crosslinking density (1% N,N-methylenebis(acrylamide) (BIS)) is shown in the bar with the checker board pattern, data for the microgel with 2% internal crosslinking density (2% BIS) is shown in the bar with black diagonal stripes, data for the microgel with 4% internal crosslinking density (4% BIS) is shown in the bar with the grey diagonal stripes, data for the microgel with 7% internal crosslinking density (7% BIS) is shown in the bar with the horizontal stripes), and data for cells cultured on a glass slide in the absence of a microgel (Glass) is shown in the bar with the dots. *$p<0.05$.

Discussion HDF cells were selected as an exemplary cell type for culturing on the printed bio-inks since they represent the majority of cells in the epidermis and thus, are major players in wound healing. FIG. 5A shows exemplary images of nHDF cells cultured onto printed patters of bio-ink. As indicated in FIGS. 5B and 5C, as the internal crosslinking density of the microgel particles increases, so does cell area and cellular migration velocities. In addition, it was observed that nHDFs begin to grow towards and along a printed bio-ink line. In summary, the printing of micropatterns of colloidal bio-ink provides the ability to promote cell attachment and migration through response to material properties. The printing of varying patterns and/or varying bio-ink compositions provides the ability to control growth and attachment of cells to aid in modular tissue engineering.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A bio-ink composition comprising:
   (a) a bio-compatible micro- or nanogel, wherein the bio-compatible micro- or nanogel comprises a poly(N-isopropylacrylamide) (poly-NIPam) polymer, wherein said poly-NIPam polymer is a copolymer of N-isopropylacrylamide, acrylic acid, and a crosslinking agent;
   (b) a liquid carrier;
   (c) about 10 volume (vol) % to about 30 vol % of a viscosity control agent, wherein the viscosity control agent is a poly(ethylene glycol) (PEG); and
   (d) 0 vol % to 50 vol % of a surface tension control agent; wherein the bio-ink composition comprises about 0.2 mg/ml to about 2 mg/ml of the micro- or nanogel.

2. The bio-ink composition of claim 1, wherein the crosslinking agent is N,N-methylenebisacrylamide (BIS) and/or cystamine bisacrylamide.

3. The bio-ink composition of claim 2, wherein the poly-NIPam polymer comprises a monomeric content comprising about 90% NIPam.

4. The bio-ink composition of claim 3, wherein the monomeric content comprises about 4% BIS.

5. The bio-ink composition of claim 1, wherein the bio-ink composition comprises about 2 mg/ml of the bio-compatible microgel.

6. The bio-ink composition of claim 1, wherein the bio-compatible micro- or nanogel has an average swollen particle diameter of between about 100 nanometers (nm) and about 10 microns (μm).

7. The bio-ink composition of claim 6, wherein the average swollen particle diameter is between about 500 nm and about 700 nm.

8. The bio-ink composition of claim 1, wherein the PEG has a weight average molecular weight (Mw) between about 100 Da and about 8,000 kDa.

9. The bio-ink composition of claim 8, wherein the bio-ink composition comprises between about 10 vol % PEG and about 20 vol % PEG.

10. The bio-ink composition of claim 8, wherein the PEG is PEG400.

11. The bio-ink composition of claim 1, wherein the surface tension agent comprises one or more agent selected from the group consisting of a surfactant and an ionic liquid.

12. The bio-ink composition of claim 11, wherein the surfactant is selected from the group consisting of sodium dodecyl sulfate (SDS), hexamethyldisilazane (HMDS), [7-hydroxy-9H-(1,2-dichloro-9,9-dimethylacridin-2-one)] (DDOA), and a sorbitan ester.

13. The bio-ink composition of claim 1, wherein the liquid carrier comprises one of the group consisting of water, saline, phosphate buffered saline (PBS), and cell culture media.

14. The bio-ink composition of claim 1, wherein the bio-ink composition further comprises one or more additional component selected from the group consisting of a metabolite, a growth factor, a cytokine, a chemokine, a CD antigen, neurotrophin, a hormone, an enzyme, a viral antigen, a bacterial antigen, a recombinant protein, a natural protein, a monoclonal antibody, a polyclonal antibody, a donor blood serum protein, a donor blood plasma protein, an antimicrobial agent, a small molecule drug, and a cell.

* * * * *